(12) United States Patent
Ozawa et al.

(10) Patent No.: US 10,490,729 B2
(45) Date of Patent: Nov. 26, 2019

(54) PIEZOELECTRIC ELEMENT, ULTRASOUND PROBE AND ULTRASOUND IMAGING APPARATUS

(71) Applicant: Konica Minolta, Inc., Tokyo (JP)

(72) Inventors: Masashi Ozawa, Kanagawa (JP); Hisashi Minemoto, Osaka (JP); Junichi Kato, Osaka (JP); Koetsu Saito, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 408 days.

(21) Appl. No.: 15/622,704

(22) Filed: Jun. 14, 2017

(65) Prior Publication Data
US 2017/0365771 A1    Dec. 21, 2017

(30) Foreign Application Priority Data
Jun. 20, 2016 (JP) .................................. 2016-121715

(51) Int. Cl.
| | | |
|---|---|---|
| H01L 41/18 | (2006.01) | |
| A61B 8/00 | (2006.01) | |
| B06B 1/06 | (2006.01) | |
| G01S 7/52 | (2006.01) | |
| H01L 41/047 | (2006.01) | |
| H01L 41/113 | (2006.01) | |

(52) U.S. Cl.
CPC ............ *H01L 41/18* (2013.01); *A61B 8/4444* (2013.01); *B06B 1/0607* (2013.01); *G01S 7/52079* (2013.01); *H01L 41/047* (2013.01); *H01L 41/1132* (2013.01)

(58) Field of Classification Search
CPC ... H01L 41/18; H01L 41/1132; H01L 41/047; A61B 8/444; B06B 1/0607
See application file for complete search history.

(56) References Cited

U.S. PATENT DOCUMENTS

| | | | | |
|---|---|---|---|---|
| 8,119,022 | B2 * | 2/2012 | Lee ............................ | C30B 1/02 252/62.9 PZ |
| 2004/0232805 | A1 * | 11/2004 | Ebigase ................ | H01L 41/083 310/358 |

(Continued)

FOREIGN PATENT DOCUMENTS

| | | |
|---|---|---|
| JP | 2006188414 A | 7/2006 |
| JP | 3839838 B2 * | 11/2006 |
| JP | 5063606 B2 | 10/2012 |

*Primary Examiner* — J. San Martin
(74) *Attorney, Agent, or Firm* — Lucas & Mercanti, LLP

(57) ABSTRACT

The ultrasound probe includes a piezoelectric element including a piezoelectric composition and an electrode that applies a voltage to the piezoelectric composition. The piezoelectric composition has piezoelectric characteristics expressed by any coordinates included in a region formed by a polyhedron having a plurality of predetermined points as vertexes in Cartesian coordinates ($k_{eff}$, $\varepsilon_{33}^S$, $E_c$) including variables $k_{eff}$, $\varepsilon_{33}^S$ and $E_c$.

20 Claims, 9 Drawing Sheets

(56) References Cited

U.S. PATENT DOCUMENTS

2015/0141834 A1* 5/2015 Minemoto ............ C04B 35/462
                                                    600/459
2018/0248106 A1* 8/2018 Ishizaki ................ C04B 35/26
2018/0248107 A1* 8/2018 Teranishi ............. C01G 23/006

* cited by examiner

PIEZOELECTRIC ELEMENT, ULTRASOUND PROBE AND ULTRASOUND IMAGING APPARATUS

CROSS REFERENCE TO RELATED APPLICATIONS

This application is entitled to and claims the benefit of Japanese Patent Application No. 2016-121715, filed on Jun. 20, 2016, the disclosure of which including the specification, drawings and abstract is incorporated herein by reference in its entirety.

BACKGROUND OF THE INVENTION

1. Field of the Invention

The present invention relates to a piezoelectric element, an ultrasound probe, and an ultrasound imaging apparatus having the ultrasound probe.

2. Description of Related Art

An ultrasound probe in an ultrasound imaging apparatus to be utilized in the medical field has a piezoelectric element including a piezoelectric composition and an electrode that applies a voltage to the piezoelectric composition. In the ultrasound imaging apparatus, the piezoelectric composition is vibrated by an electrical signal to thereby generate ultrasound to be transmitted. The ultrasound reflected in a subject is received by the ultrasound probe. Thus, the ultrasound imaging apparatus can obtain an ultrasound image of the subject.

The ultrasound probe preferably includes a piezoelectric composition having a high relative permittivity, a coercive electric field and an electromechanical coupling coefficient from the viewpoint of realizing an ultrasound probe having a high sensitivity to ultrasound. As an example of such an ultrasound probe, an ultrasound probe is known which includes a piezoelectric composition having a perovskite structure including zirconium in a predetermined composition (see, for example, Japanese Patent No. 5063606). The piezoelectric composition of the ultrasound probe has a relative permittivity of 4,000 or more and a coercive electric field of about 5.3 to 10 kV/cm. The relative permittivity of the piezoelectric composition described in Japanese Patent No. 5063606 here means a value measured at a sufficiently low frequency (usually 1 kHz) after a polarization treatment, namely, a relative permittivity ($\varepsilon^T$) in a free state.

As another example of the ultrasound probe, a piezoelectric element is known which includes a piezoelectric composition being a $BiScO_3$-based solid solution (see, for example, Japanese Patent Application Laid-Open No. 2006-188414). The relative permittivity of the piezoelectric composition of the piezoelectric element is also measured at a low frequency.

There is a case where a piezoelectric composition having a small thickness is used, for example, a case where an acoustic back layer acoustically coupled to a piezoelectric element is included, a case where ultrasound having a high center frequency (for example, center frequency: 7 MHz or more) is used, or a case where a piezoelectric element is layered. In such a case, there is demanded an ultrasound probe that can be driven at a high driving voltage and that has a higher sensitivity to ultrasound than a conventional ultrasound probe, from the viewpoint of a further increase in performance of an ultrasound imaging apparatus.

In the above case, the piezoelectric composition is in a substantially bound state. That is, the piezoelectric composition of an actual ultrasound probe is fixed to other member (for example, acoustic back layer) by an adhesive or the like, and is thus in a bound state to some extent. Furthermore, when the frequency of ultrasound is in the vicinity of the antiresonant frequency or is higher than the antiresonant frequency, the piezoelectric composition is in a substantially bound state. Therefore, not relative permittivity $\varepsilon^T$ (hereinafter, also referred to as "free relative permittivity") in a free state after a polarization treatment, but relative permittivity $\varepsilon^S$ (hereinafter, also referred to as "bound relative permittivity") in a bound state after a polarization treatment is important for the design of an ultrasound probe.

The design of a probe in consideration of a free relative permittivity cannot sometimes provide any ultrasound probe having a piezoelectric element having a small thickness, the probe realizing desired piezoelectric characteristics and having a sufficient sensitivity to ultrasound. As is clear from the above PTLs, an ultrasound probe has been conventionally known which includes a piezoelectric element having a piezoelectric composition focused on a free relative permittivity.

While an ultrasound probe is preferably high in electromechanical coupling coefficient with respect to a vibration mode in a direction (longitudinal direction) parallel with the polarization direction (electric field direction), it is preferably low in electromechanical coupling coefficient with respect to a vibration mode in a direction (lateral direction) perpendicular to the polarization direction (electric field direction). As is clear from Japanese Patent Application Laid-Open No. 2006-188414, a piezoelectric component for a low frequency, focused on the electromechanical coupling coefficients ($k_p$, $k_{31}$) in the lateral direction, such as a piezoelectric speaker or a piezoelectric pump, has been conventionally known as a piezoelectric element having a PMN-PZT-based piezoelectric composition partially replaced with $BiScO_3$. Any piezoelectric element including the piezoelectric composition, however, is not known at all which is designed in consideration of bound relative permittivity $\varepsilon_{33}^S$ and electromechanical coupling coefficient $k_{33}$ in an ultrasound region (PMN and PZT represent $Pb(Mg_{1/3}Nb_{2/3})O_3$ and $Pb(ZrTi)O_3$, respectively).

Furthermore, no ultrasound probe has been found, which is focused on a bound relative permittivity, and the electromechanical coupling coefficient or the effective electromechanical coupling coefficient in the longitudinal direction and which includes a piezoelectric composition sufficiently high in all of a bound relative permittivity, a coercive electric field and an effective electromechanical coupling coefficient. Accordingly, a piezoelectric composition having a small thickness cannot sometimes impart a sufficient sensitivity to ultrasound.

SUMMARY OF THE INVENTION

A first object of the present invention is to provide a piezoelectric element and an ultrasound probe excellent in sensitivity to ultrasound even when a piezoelectric composition having a small thickness is adopted. A second object of the present invention is to provide an ultrasound imaging apparatus having the ultrasound probe.

In order to achieve at least one of the above objects, an ultrasound probe according to a first aspect of the present invention is an ultrasound probe including a piezoelectric element including a piezoelectric composition and an electrode that applies a voltage to the piezoelectric composition, and an acoustic back layer acoustically coupled to the piezoelectric element on a back surface of the piezoelectric element, in which the piezoelectric composition has piezoelectric characteristics expressed by any coordinates included in a region formed by a polyhedron having point A1 to point A18 shown below as vertexes in Cartesian coordinates ($k_{eff}$, $\varepsilon_{33}^S$, $E_c$) including variables $k_{eff}$, $\varepsilon_{33}^S$ and $E_c$ when an effective electromechanical coupling coefficient, a bound relative permittivity and a coercive electric field thereof are defined as $k_{eff}$, $\varepsilon_{33}^S$ and $E_c$ (kV/cm), respectively:

Point A1 (0.5, 2200, 18)
Point A2 (0.5, 1400, 18)
Point A3 (0.7, 600, 18)
Point A4 (0.9, 600, 18)
Point A5 (0.9, 2200, 18)
Point A6 (0.5, 2200, 15)
Point A7 (0.5, 1400, 15)
Point A8 (0.7, 600, 15)
Point A9 (0.9, 600, 15)
Point A10 (0.65, 2200, 10)
Point A11 (0.65, 1400, 10)
Point A12 (0.8, 600, 10)
Point A13 (0.9, 600, 10)
Point A14 (0.75, 2200, 7)
Point A15 (0.75, 1400, 7)
Point A16 (0.8, 1000, 7)
Point A17 (0.9, 600, 7)
Point A18 (0.9, 2200, 7)

In order to achieve at least one of the above objects, an ultrasound probe according to a second aspect of the present invention is an ultrasound probe including a piezoelectric element including a plurality of piezoelectric compositions and an electrode that applies a voltage to each of the plurality of piezoelectric compositions, a layer of each of the piezoelectric compositions and the electrode being alternately stacked, in which the piezoelectric composition has piezoelectric characteristics expressed by any coordinates included in a region formed by a polyhedron having point B1 to point B14 shown below as vertexes in Cartesian coordinates ($k_{eff}$, $\varepsilon_{33}^S$, $E_c$) including variables $k_{eff}$, $\varepsilon_{33}^S$ and $E_c$ when an effective electromechanical coupling coefficient, a bound relative permittivity and a coercive electric field thereof are defined as $k_{eff}$, $\varepsilon_{33}^S$ and $E_c$ (kV/cm), respectively:

Point B1 (0.5, 2200, 18)
Point B2 (0.5, 600, 18)
Point B3 (0.9, 600, 18)
Point B4 (0.9, 2200, 18)
Point B5 (0.5, 2200, 15)
Point B6 (0.5, 600, 15)
Point B7 (0.65, 2200, 9)
Point B8 (0.65, 1000, 9)
Point B9 (0.75, 600, 9)
Point B10 (0.9, 600, 9)
Point B11 (0.8, 2200, 7)
Point B12 (0.8, 1000, 7)
Point B13 (0.9, 1000, 7)
Point B14 (0.9, 2200, 7)

In order to achieve at least one of the above objects, an ultrasound probe according to a third aspect of the present invention is an ultrasound probe including a piezoelectric element including a single-layer piezoelectric composition and an electrode that applies a voltage to the piezoelectric composition, and no acoustic back layer to be acoustically coupled to the piezoelectric element on a back surface of the piezoelectric element, in which the piezoelectric composition has piezoelectric characteristics expressed by any coordinates included in a region formed by a polyhedron having point C1 to point C18 shown below as vertexes in Cartesian coordinates ($k_{eff}$, $\varepsilon_{33}^S$, $E_c$) including variables $k_{eff}$, $\varepsilon_{33}^S$ and $E_c$ when an effective electromechanical coupling coefficient, a bound relative permittivity and a coercive electric field thereof are defined as $k_{eff}$, $\varepsilon_{33}^S$ and $E_c$ (kV/cm), respectively:

Point C1 (0.55, 2200, 18)
Point C2 (0.55, 1400, 18)
Point C3 (0.75, 600, 18)
Point C4 (0.9, 600, 18)
Point C5 (0.9, 2200, 18)
Point C6 (0.55, 2200, 13)
Point C7 (0.55, 1400, 13)
Point C8 (0.75, 600, 13)
Point C9 (0.9, 600, 13)
Point C10 (0.6, 2200, 10)
Point C11 (0.6, 1400, 10)
Point C12 (0.8, 600, 10)
Point C13 (0.9, 600, 10)
Point C14 (0.75, 2200, 7)
Point C15 (0.75, 1400, 7)
Point C16 (0.8, 1200, 7)
Point C17 (0.9, 1200, 7)
Point C18 (0.9, 2200, 7)

In order to achieve at least one of the above objects, a piezoelectric element according to a fourth aspect of the present invention includes a piezoelectric composition including, as a main component, a composition represented by the following general formula, and an electrode that applies a voltage to the piezoelectric composition, in which the piezoelectric composition satisfies the following expressions (1) to (3) when an electromechanical coupling coefficient, a bound relative permittivity and a coercive electric field thereof are defined as $k_{33}$, $\varepsilon_{33}^S$ and $E_c$ (kV/cm), respectively:

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\}$$

in which A represents Ba or Sr, M1 represents Mg, or Mg and Zn, and the following expressions (4) to (8) are satisfied:

$$k_{33} \geq 0.65 \tag{1}$$

$$\varepsilon_{33}^S \geq 1000 \tag{2}$$

$$E_c \geq 12 \tag{3}$$

$$0 \leq a2 \leq 0.1 \tag{4}$$

$$a1 + a2 = 1 \tag{5}$$

$$x + y + z = 1 \tag{6}$$

$$0.1 \leq x \leq 0.375 \tag{7}$$

$$0.5 \leq y/(y+z) \leq 0.64 \tag{8}$$

In order to achieve at least one of the above objects, an ultrasound imaging apparatus according to one aspect of the present invention includes the ultrasound probe.

BRIEF DESCRIPTION OF DRAWINGS

The present invention will become more fully understood from the detailed description given herein below and the appended drawings which are given by way of illustration only, and thus are not intended as a definition of the limits of the present invention, and wherein.

DESCRIPTION OF THE PREFERRED EMBODIMENTS

A piezoelectric composition forming a piezoelectric element is required to have a small thickness from the viewpoint of generating an ultrasound high in center frequency. When the coercive electric field of the piezoelectric composition is constant, the voltage that can be applied to the piezoelectric element is decreased as the thickness of the piezoelectric composition is decreased. When the coercive electric field of the piezoelectric composition is too low, a high voltage cannot be applied to the piezoelectric element, and the output of ultrasound cannot be increased. Therefore, the resulting ultrasound probe has difficulty in having an increased sensitivity. Accordingly, the piezoelectric composition of the ultrasound probe preferably has a high coercive electric field in order that the sensitivity to ultrasound is higher even when the piezoelectric composition has a small thickness.

The relative permittivity of the piezoelectric composition tends to be lower, as the coercive electric field is higher. As the relative permittivity of the piezoelectric composition is lower, a piezoelectric element using the piezoelectric composition is higher in electric impedance. The electric impedance is required to be matched with electric impedances of a transmitting circuit and a receiving circuit of an ultrasound imaging apparatus from the viewpoint of increasing the sensitivity to ultrasound. An existing ultrasound probe is often higher in the electric impedance of a piezoelectric composition than the electric impedances of the transmitting circuit and the receiving circuit, and a reduction in the electric impedance of a piezoelectric element is demanded. That is, a piezoelectric composition of an ultrasound probe preferably has a high relative permittivity from the viewpoints that the electric impedance is matched in the ultrasound probe and the sensitivity to ultrasound is increased.

As described above, the present inventors have focused on bound relative permittivity $\varepsilon^S$ instead of free relative permittivity $\varepsilon^T$, and also have focused on effective electromechanical coupling coefficient $k_{eff}$.

An object of the present invention is to realize a piezoelectric element and an ultrasound probe including a piezoelectric composition being sufficient in all of a bound relative permittivity, a coercive electric field and an effective electromechanical coupling coefficient, and having a high sensitivity to ultrasound even when the piezoelectric composition has a small thickness. Another object of the present invention is to realize an ultrasound imaging apparatus including the ultrasound probe. Hereinafter, Embodiments of the present invention are described.

[Embodiment 1]

An ultrasound probe according to Embodiment 1 includes an acoustic back layer as a structural feature.

Figure 1:
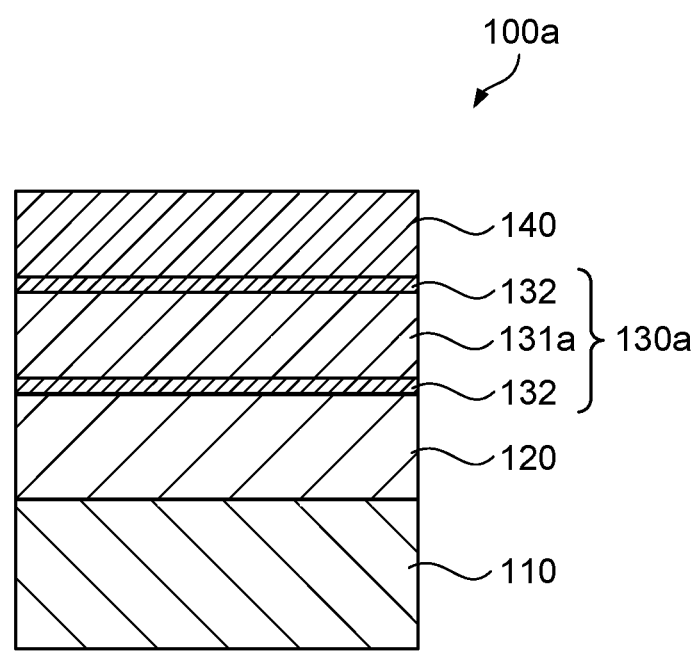
FIG. 1 illustrates a schematic cross-sectional view of one configuration example of an ultrasound probe according to Embodiment 1 of the present invention.

FIG. 1 illustrates a schematic cross-sectional view of one configuration example of an ultrasound probe according to Embodiment 1 of the present invention. Ultrasound probe 100a according to the present Embodiment includes back surface load material 110, acoustic back layer 120, piezoelectric element 130a, acoustic matching layer 140 and a flexible printed circuit (FPC, not illustrated).

Ultrasound probe 100a can be configured in the same manner as in a known ultrasound probe, except for piezoelectric element 130a. For example, an electrode is attached to piezoelectric element 130a in FPC not illustrated, and any beamforming can be performed by transmitting and receiving driving of ultrasound to be controlled in an ultrasound imaging apparatus to which ultrasound probe 100a is connected.

The center frequency of a transmitting and receiving band of ultrasound in ultrasound probe 100a according to the present Embodiment is not particularly limited. The center frequency is preferably 7 MHz or more, more preferably 10 MHz or more, further preferably 12 MHz or more from the viewpoint of an increase in the resolution of ultrasound probe 100a. The center frequency is preferably 30 MHz or less from the viewpoint of suppressing attenuation of ultrasound. The transmitting and receiving band refers to a frequency band of ultrasound to be transmitted from and received by piezoelectric element 130a. The center frequency refers to the average value of the upper limit frequency and the lower limit frequency in a frequency band where the maximum peak value of ultrasound is reduced by −6 dB.

The center frequency can be appropriately set depending on the intended use of ultrasound probe 100a. The center frequency can be increased as the thickness of piezoelectric element 130a is decreased.

(Back Surface Load Material)

Back surface load material 110 is an ultrasound absorber having an acoustic impedance higher than the acoustic impedance of piezoelectric element 130a and absorbing unnecessary ultrasound. In the present Embodiment, back surface load material 110 supports acoustic back layer 120. Back surface load material 110 is mounted on a surface (rear surface, back surface) of piezoelectric element 130a, the surface being opposite to a surface of piezoelectric element 130a on the side capable of transmitting ultrasound to and receiving ultrasound from a subject (for example, a living body), thereby absorbing ultrasound generated on a surface opposite to the subject.

Examples of the material of back surface load material 110 include natural rubber, ferrite rubber, an epoxy resin, a silicone resin, a thermoplastic resin, and a resin-based composite obtained by press molding of a mixture of at least any of such materials with a powder of tungsten oxide, titanium oxide, ferrite, or the like. Other examples of the material of back surface load material 110 include a material obtained by pulverizing the resin-based composite, mixing it with other material such as the thermoplastic resin or the epoxy resin, and curing the resulting mixture.

Examples of the thermoplastic resin include vinyl chloride, polyvinyl butyral, an ABS resin, polyurethane, polyvinyl alcohol, polyethylene, polypropylene, polyacetal, polyethylene terephthalate, a fluororesin, polyethylene glycol and a polyethylene terephthalate-polyethylene glycol copolymer. The material of back surface load material 110 is particularly preferably a resin-based composite, further particularly preferably a rubber composite material or an epoxy resin-based composite.

Other compounding agent may also be, if necessary, added to back surface load material 110. For example, an inorganic material such as Macor glass or glass, or a porous material having pores may also be added to back surface load material 110 from the viewpoint of adjusting the acoustic impedance of back surface load material 110.

The shape of back surface load material 110 can be appropriately determined depending on the shapes of piezoelectric element 130a, ultrasound probe 100a including piezoelectric element 130a, and the like.

The thickness of back surface load material 110 is preferably in the range from 1 to 30 mm, more preferably in the range from 1 to 10 mm.

Herein, back surface load material 110 and FPC described below can be bonded to each other by, for example, an adhesive (for example, an epoxy-based adhesive) commonly used in the technical field.

(Acoustic Back Layer)

Acoustic back layer 120 is disposed facing the back surface of piezoelectric element 130a, and changes the vibration mode of piezoelectric element 130a. Acoustic back layer 120 is acoustically coupled to piezoelectric element 130a. The "front surface" of the piezoelectric element refers to a surface disposed on the side capable of transmitting ultrasound to and receiving ultrasound from a subject, and the "back surface" of the piezoelectric element refers to a surface of the piezoelectric element, disposed opposite to the front surface. Acoustic back layer 120 may have an acoustic impedance different from or comparable with the acoustic impedance of piezoelectric composition 131a.

When acoustic back layer 120 serves as an acoustic reflection layer, the acoustic impedance of acoustic back layer 120 is higher than the acoustic impedance of piezoelectric composition 131a. In such a case, acoustic back layer 120 is mounted on the back surface of piezoelectric element 130a, and reflects ultrasound transmitted opposite to the subject (the back surface of piezoelectric element 130a). Ultrasound probe 100a preferably has acoustic back layer 120 from the viewpoint of increasing the sensitivity to ultrasound.

The material of acoustic back layer 120 is not particularly limited. Examples of the material of acoustic back layer 120 include tungsten and tantalum. Acoustic back layer 120 may also include a piezoelectric composition not subjected to a polarization treatment. In particular, when acoustic back layer 120 serves as an acoustic reflection layer, the material of acoustic back layer 120 is preferably tungsten carbide in terms of reflection efficiency.

The thickness of acoustic back layer 120 is appropriately determined depending on the center frequency, acoustic design, and the like. The thickness of acoustic back layer 120 is preferably in the range from 0.01 to 1 mm, more preferably in the range from 0.02 to 0.4 mm.

(Piezoelectric Element)

Piezoelectric element 130a can convert an electrical signal to a mechanical vibration, and can also convert a mechanical vibration to an electrical signal. Thus, piezoelectric element 130a can transmit and receive ultrasound.

Herein, piezoelectric element 130a and acoustic back layer 120 are preferably at least partially bonded to each other by an adhesion layer from the viewpoint of an increase in adhesiveness of piezoelectric element 130a and acoustic back layer 120. For example, a silicone-based adhesive or an epoxy-based adhesive can be used as the material of the adhesion layer.

The shape of piezoelectric element 130a can be appropriately set depending on the intended use. For example, the shape of piezoelectric element 130d may be a rectangular parallelepiped shape or a cylindrical shape. The shape of piezoelectric element 130a may also be a shape where the thickness is constant from the center portion toward the peripheral portion, or may also be a hanafy lens shape where the thickness is decreased from the center portion toward the peripheral portion. The shape of piezoelectric element 130a is preferably a hanafy lens shape from the viewpoint of increasing the sensitivity to ultrasound.

Piezoelectric element 130a according to the present Embodiment includes piezoelectric composition 131a and electrode 132 that applies a voltage to piezoelectric composition 131a. In the present Embodiment, two electrodes 132 are disposed on both surfaces of single-layer piezoelectric composition 131a so as to be opposite to each other with piezoelectric composition 131a interposed.

Piezoelectric composition 131a may be any as long as it has piezoelectricity, and may be ceramics, oriented ceramics, an inorganic/organic composite, or a single crystal.

Figure 2:
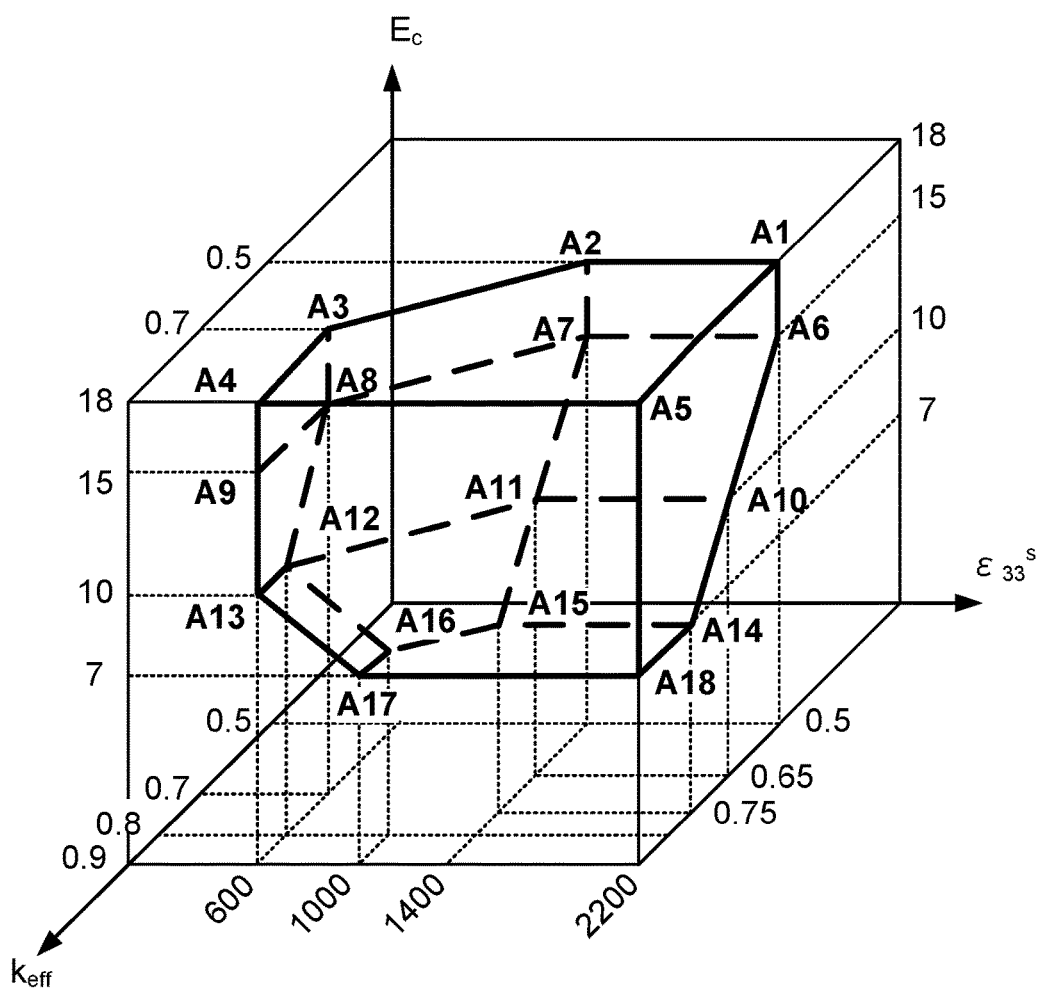
FIG. 2 illustrates a schematic view illustrating piezoelectric characteristics of a piezoelectric composition according to Embodiment 1 of the present invention.

FIG. 2 illustrates a schematic view illustrating piezoelectric characteristics of piezoelectric composition 131a according to Embodiment 1. Piezoelectric composition 131a, as illustrated in FIG. 2, has piezoelectric characteristics expressed by any coordinates included in a region formed by polyhedron 1 having point A1 to point A18 shown below as vertexes in Cartesian coordinates ($k_{eff}$, $\varepsilon_{33}^S$, $E_c$) including variables $k_{eff}$, $\varepsilon_{33}^S$ and $E_c$ when the effective electromechanical coupling coefficient, the bound relative permittivity and the coercive electric field thereof are defined as $k_{eff}$, $\varepsilon_{33}^S$ and $E_c$ (kV/cm), respectively:

Point A1 (0.5, 2200, 18)
Point A2 (0.5, 1400, 18)
Point A3 (0.7, 600, 18)
Point A4 (0.9, 600, 18)
Point A5 (0.9, 2200, 18)
Point A6 (0.5, 2200, 15)
Point A7 (0.5, 1400, 15)
Point A8 (0.7, 600, 15)
Point A9 (0.9, 600, 15)
Point A10 (0.65, 2200, 10)
Point A11 (0.65, 1400, 10)
Point A12 (0.8, 600, 10)
Point A13 (0.9, 600, 10)
Point A14 (0.75, 2200, 7)
Point A15 (0.75, 1400, 7)
Point A16 (0.8, 1000, 7)
Point A17 (0.9, 1000, 7)
Point A18 (0.9, 2200, 7)

If piezoelectric composition 131a is too low in at least one of $k_{eff}$, $\varepsilon_{33}^S$ and $E_c$ to have piezoelectric characteristics expressed by any coordinates included in a region formed by polyhedron 1, a sufficient sensitivity to ultrasound is not achieved. Piezoelectric composition 131a which is too high in at least one of $k_{eff}$, $\varepsilon_{33}^S$ and $E_c$ to have piezoelectric characteristics expressed by any coordinates included in a region formed by polyhedron 1 is not preferable because of being difficult to actually produce.

"Effective electromechanical coupling coefficient $k_{eff}$" here represents an effective electromechanical coupling coefficient (coefficient representing the conversion ability between the electric energy applied to piezoelectric composition 131a, and the mechanical energy) possessed by piezoelectric composition 131a incorporated into ultrasound probe 100a. "$k_{eff}$" is a value depending on the vibration mode of piezoelectric composition 131a in ultrasound probe 100a, and the structure of ultrasound probe 100a.

"$k_{eff}$" can be measured with respect to piezoelectric composition 131a processed into a shape for actual use as an ultrasound probe, according to a resonance-antiresonance method with a commercially available impedance analyzer.

"$k_{eff}$" can be adjusted by the composition of piezoelectric composition 131a, the relative density to the theoretical density of piezoelectric composition 131a (when piezoelectric composition 131a is ceramics), the crystal orientation of piezoelectric composition 131a, and the like. As the composition of piezoelectric composition 131a is closer to the morphotropic phase boundary (MPB), "$k_{eff}$" tends to be higher. In addition, as the relative density of piezoelectric composition 131a is higher, "$k_{eff}$" tends to be higher.

"Bound relative permittivity $\varepsilon_{33}^S$" represents the relative permittivity along with direction 33 when the strain of piezoelectric composition 131a is constant, and it means a relative permittivity at a sufficiently high frequency (for example, center frequency: 7 MHz or more) compared with the antiresonant frequency. In ultrasound probe 100a, a frequency equal to or higher than the frequency ranging from the resonant frequency to the antiresonant frequency is used, and piezoelectric composition 131a is substantially bound because of being fixed to other member by an adhesive or the like. Therefore, an important parameter for the ultrasound probe is not free relative permittivity $\varepsilon_{33}^T$, but bound relative permittivity $\varepsilon_{33}^S$.

"$\varepsilon_{33}^S$" can be measured by use of a commercially available impedance analyzer, with respect to rod-like (shape 33) piezoelectric composition 131a (for example, a piezoelectric composition having a size of 1 mm×1 mm×3 mm, polarized in the longitudinal direction) that is higher in the length in a direction parallel with the polarization direction than the length in a direction perpendicular to the polarization direction. The frequency to be used here is a sufficiently higher frequency (for example, 10 MHz) than the antiresonant frequency of mode 33. The adjustment method of $\varepsilon_{33}^S$ is described below.

Furthermore, "coercive electric field $E_c$" represents a voltage to be applied which is necessary for application of a voltage in a reverse direction to the polarization direction of the remaining polarization in piezoelectric composition 131a to allow the remaining polarization in piezoelectric composition 131a to disappear.

"$E_c$" can be measured by, for example, the following method. First, an electric field ranging from 0 kV/cm to 40 kV/cm is applied to piezoelectric composition 131a and an electric field ranging from 40 kV/cm to −40 kV/cm is continuously applied thereto by use of a ferroelectric characteristic evaluation system (manufactured by Leadtech) at room temperature, to measure the hysteresis of the amount of polarization (μC/cm²) to the electric field intensity (kV/cm) in continuous application of a voltage of −40 kV/cm to 40 kV/cm. The coercive electric field can be determined from the electric field intensity value at an amount of polarization of 0 in the resulting hysteresis curve.

The thickness of piezoelectric composition 131a can be appropriately set depending on the center frequency of ultrasound, the frequency constant of piezoelectric composition 131a, the acoustic design, and the like. The thickness of piezoelectric composition 131a is preferably small from the viewpoint of realizing a high center frequency. For example, the thickness of piezoelectric composition 131a is preferably in the range from 0.02 to 1 mm, more preferably in the range from 0.03 to 0.4 mm. When the center frequency is 10 MHz, the thickness of piezoelectric composition 131a is, for example, in the range from 0.04 to 0.2 mm.

From the viewpoint of realizing a high sensitivity to ultrasound, piezoelectric composition 131a preferably satisfies the following expressions when the electromechanical coupling coefficient, the bound relative permittivity and the coercive electric field thereof are defined as $k_{33}$, $\varepsilon_{33}^S$ and $E_c$ (kV/cm), respectively:

$$k_{33} \geq 0.65$$

$$\varepsilon_{33}^S \geq 1000$$

$$E_c \geq 12$$

"Electromechanical coupling coefficient $k_{33}$" here is a coefficient representing the conversion ability between the electric energy applied to the piezoelectric composition, and the mechanical energy, and is a value intrinsic to the piezoelectric composition. In the present Embodiment, the $k_{eff}$ value is about $0.9 \times k_{33}$ to $1 \times k_{33}$. Bound relative permittivity $\varepsilon_{33}^S$ and coercive electric field a are the same as $\varepsilon_{33}^S$ and $E_c$ described above, respectively.

"$k_{eff}$" can be measured with respect to rod-like (shape 33) piezoelectric composition 131a (for example, a piezoelectric composition having a size of 1 mm×1 mm×3 mm, polarized in the longitudinal direction) that is higher in the length in a direction along with the polarization direction than the length in a direction perpendicular to the polarization direction, according to a resonance-antiresonance method with a commercially available impedance analyzer. The adjustment method of $k_{33}$ is described below.

The upper limit of $k_{33}$ is not particularly limited. The upper limit of $k_{33}$ can be appropriately determined within the scope where piezoelectric composition 131a can be produced.

The composition of piezoelectric composition 131a can be appropriately changed as long as at least one of the effects of the present Embodiment is obtained. Piezoelectric composition 131a may be produced by a production method described below, or may be a ready-made product. Piezoelectric composition 131a preferably includes, as a main component, a composition represented by the following general formula (1), more preferably includes, as a main component, a composition represented by the following general formula (2), from the viewpoint of realizing a high sensitivity to ultrasound. The content of the main component relative to piezoelectric composition 131a is, for example, 0 to 20 parts by mass (more than 0 parts by mass and 20 parts by mass or less). When piezoelectric composition 131a is here an inorganic/organic composite, the content of the main component is defined as the content under the assumption that the proportion of only an inorganic substance except for an organic substance is 100 parts by mass.

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\} \quad (1)$$

In the general formula (1), A represents Ba or Sr, M1 represents Mg, or Mg and Zn, and the following expressions are satisfied. When M1 represents Mg and Zn, the ratio of Mg and Zn is not particularly limited, and is, for example, 10:0 to 5:5.

$$0 \leq a2 \leq 0.1$$

$$a1+a2=1$$

$$x+y+z=1$$

$$0.1 \leq x \leq 0.375$$

$$0.5 \leq y/(y+z) \leq 0.64$$

$$x[(Pb_{a1}A_{a2})\{(M1_{1/3}Nb_{2/3})O_3\}]\text{-}y\{(Pb_{a1}A_{a2})TiO_3\}\text{-}z \\ [R1\{(Pb_{a1}A_{a2})ZrO_3\}\text{---}R2(BiScO_3)] \quad (2)$$

In the general formula (2), A represents Ba or Sr, M1 represents Mg, or Mg and Zn, and the following expressions are satisfied. When M1 represents Mg and Zn, the ratio of Mg and Zn is not particularly limited, and is, for example, 10:0 to 5:5.

$$0 \leq a2 \leq 0.1$$

$$a1+a2=1$$

$$x+y+z=1$$

$$0.1 \leq x \leq 0.25$$

$$0.5 \leq y/(y+z) \leq 0.64$$

$$0 < R2 \leq 0.25$$

In the general formulae (1) and (2), the values of a1, a2, x, y, z and R2 can be appropriately set as long as at least one of the effects of the present Embodiment is obtained. If barium (Ba) or strontium (Sr) is excessively added to piezoelectric composition 131a, $k_{33}$ may be excessively lower, and therefore a2 is preferably 0.1 or less. The present inventors have also first found that the inclusion of $BiScO_3$ in piezoelectric composition 131a is effective for increasing $k_{33}$ ($k_{eff}$) and piezoelectric constant $d_{33}$ as piezoelectric characteristics in the polarization direction with $\varepsilon_{33}^S$ being kept.

Each microcrystal of piezoelectric composition 131a may be ceramics oriented in a specific plane orientation (so-called oriented ceramics) or may be a single crystal having a specific plane orientation. The specific plane orientation, while it may be in any orientation, is preferably (001), (110) or (111) in terms of a pseudocubic crystal from the viewpoint of more enhancing piezoelectricity.

A known method can be used for an orientation method of ceramics, and for example, a TGG method in which a seed particle (or referred to as a template particle) and a matrix particle are used, an RTGG method including a reaction to be performed halfway, or a magnetic field orientation method and the like, can be used.

The contents of various elements in piezoelectric composition 131a can be calculated from the amounts of raw materials loaded, in the case of ceramics, for example. More precisely, inductively coupled plasma (ICP) emission spectrometry or the like can be used. In the case of a single crystal, any difference between the composition in loading and the composition of a crystal produced may occur, and therefore the contents can be determined by a method with an electron probe micro analyzer (EPMA), ICP emission spectrometry, or the like. The crystal system of the compound in piezoelectric composition 131a can be confirmed by, for example, an X-ray diffraction method. The plane orientation in piezoelectric composition 131a can be confirmed by, for example, an X-ray diffraction method. The degree of orientation can be confirmed by, for example, a Lotgering method or a rocking curve method.

Piezoelectric composition 131a may contain, if necessary, other accessory component. Examples of the accessory component include impurities (a donor and an acceptor), a seed particle (for example, $BaTiO_3$ or $SrTiO_3$) in the case of piezoelectric composition 131a being oriented ceramics, and an additive (for example, lead oxide, bismuth oxide) for suppression of evaporation of Pb and Bi in production (sintering) of piezoelectric composition 131a. The content of the accessory component in piezoelectric composition 131a is, for example, 0 to 20 parts by mass (more than 0 parts by mass and 20 parts by mass or less). The accessory component may be partially or fully in the form of a solid solution, or may not be in the form of a solid solution. When the accessory component is not in the form of a solid solution, the accessory component is present as a subphase (seed particle including a subphase) in the piezoelectric composition.

Next, a method of producing piezoelectric composition 131a is described. The method of producing piezoelectric composition 131a includes at least a raw material preparation step of providing a raw material composition containing powders including desired elements selected from the group consisting of lead, barium, strontium, magnesium, niobium, titanium, zirconium, bismuth and scandium in a proportion depending on the composition of piezoelectric composition 131a to be produced, a heat treatment step of heating the composition to 800 to 1,300° C. to provide piezoelectric composition 131a, and a cooling step of cooling piezoelectric composition 131a to a desired temperature, preferably −20 to 40° C.

The production method can be performed in the same manner as in a common piezoelectric composition production method as long as specific conditions described below such as the types of materials and temperature conditions are satisfied. Hereinafter, the respective steps are described.

[Raw Material Preparation Step]

The raw material preparation step is a step of preparing the raw material composition, for example, a raw material powder or a molded product thereof. Hereinafter, the raw material preparation step is described with reference to specific examples. First, respective powders serving as sources of inorganic elements in piezoelectric composition 131a, for example, desired oxide(s), carbonate(s), and various acid salts, are prepared. Examples of the oxide(s) include PbO, $Pb_2O_3$, $Pb_3O_4$, $Bi_2O_3$, $TiO_2$, $ZrO_2$, $Sc_2O_3$, MgO, ZnO, $Nb_2O_5$, $MgNb_2O_6$ and $ZnNb_2O_6$. Examples of the carbonate(s) include $BaCO_3$ and $SrCO_3$.

Next, respective powders containing inorganic elements, weighed in necessary amounts, are mixed to produce a raw material powder. The method of producing the raw material powder may be any of dry and wet methods. Examples of the method include a wet pulverizing method by a ball mill, a jet mill, or the like. When a wet pulverizing method is performed by a ball mill, the raw material powder is mixed with a dispersant, and the resulting mixture is loaded into a pulverizing apparatus. Examples of the dispersant include various alcohols such as methanol and ethanol, and pure water. A pulverizing medium such as a zirconia ball is further added to a pulverizing apparatus, and mixing and pulverizing are performed, for example, until the raw material powder is made fine and substantially uniform in terms of the particle size.

Next, the pulverizing medium is taken out from the resulting mixture, and the dispersant is removed from the mixture by use of a common apparatus such as a suction filtration apparatus or a dryer to provide the raw material powder.

Next, the resulting raw material powder is placed in a vessel such as a crucible, and calcined. Such calcining can be performed at, for example, 600° C. to 1,000° C. Thus, the raw material powder can be made uniform in the composition and can be enhanced in the sintered density. The calcining, however, is not necessarily essential, and the raw material powder from which the dispersant is removed by drying may be subjected to the following molding step without being calcined, or on the contrary, may be calcined twice or more for the purposes of uniformity of the composition and an enhancement in the sintered density.

After the calcining, the raw material powder calcined may be re-pulverized. In the re-pulverizing step, a binder may be further added to the raw material powder. The binder can be added at any stage of the initial, the middle or the end of the re-pulverizing step. When the binder is added, the resulting mixture is, for example, dried again. Examples of the binder include polyvinyl alcohol (PVA) and polyvinyl butyral (PVB).

Next, the mixture is molded to provide a molded product. Such molding is performed using, for example, a machine commonly used, and the mixture is molded into, for example, a cylindrical pellet. The pellet has, for example, a diameter of about 10 to 50 mm and a thickness of about 1 to 5 mm. In the case of an array type ultrasound probe, the mixture can be molded to a plate-like pellet having a longitudinal width of about 10 to 20 mm, a lateral width of about 30 to 70 mm and a thickness of about 1 to 5 mm.

Finally, the resulting molded product is placed in an electric furnace, and heated to 500 to 750° C. for about several hours to 20 hours. Such heating allows the binder to be removed from the molded product. Thus, the molded product, as one example of the raw material composition, is obtained by molding the raw material powder into a predetermined shape. The raw material preparation step is thus completed.

The molded product is not be necessarily calcined, as described above. While the raw material preparation step is described as that in a case of a common solid phase method, the step can also be performed by, for example, a method utilizing a hydrothermal synthesis method, or a method using an alkoxide as a starting material. In such a case, the molded product not calcined can be obtained.

[Heat Treatment Step]

The heat treatment step is a step of placing the raw material composition in a heating furnace such as a crucible and heating it to 800 to 1,300° C. as a treatment temperature, more preferably 950 to 1,250° C. The heating rate is usually 50 to 300° C./hour, depending on the size of the raw material composition. The heat treatment step provides a sintered body of the piezoelectric composition. The heating rate may be constant or varied in the heat treatment step. The heating rate can be represented as a representative value (for example, average value).

The treatment time in the heat treatment step has been conventionally about 5 minutes to 4 hour in general. The treatment time is preferably 6 to 3,000 hours when piezoelectric composition 131a is a single crystal. The reason is because the heat treatment step serves as a crystal growth step when piezoelectric composition 131 is particularly a single crystal. When piezoelectric composition 131a is oriented ceramics or ceramics (polycrystal), the treatment time is preferably 5 minutes to 300 hours, more preferably 1 hour to 200 hours.

The treatment temperature may or may not be constant. For example, the treatment temperature may be gradually dropped in the heat treatment step. Such dropping of the treatment temperature is particularly effective when piezoelectric composition 131a to be obtained is a single crystal. For example, in the case of 2-stage sintering, such sintering is performed at a high temperature for only a slightly short time at the initial stage, and thereafter at a temperature lower than the initial temperature by about 50 to 250° C. Also in such a case, the treatment temperature is not constant.

[Cooling Step]

The cooling step is a step of cooling piezoelectric composition 131a obtained in the heat treatment step to a desired temperature, for example, −20 to 40° C., more specifically room temperature. The cooling rate in the cooling step is preferably 0.1 to 200° C./min from the viewpoints of productivity and prevention of pinning of a domain. The cooling rate in the cooling step may be constant or varied. The cooling rate can be represented as a representative value (for example, average value).

Piezoelectric composition 131a is suitably used in piezoelectric element 130a. Piezoelectric element 130a includes piezoelectric composition 131a and electrode 132 that applies a voltage to piezoelectric composition 131a, and is formed into a predetermined form in the same manner as in a known piezoelectric composition except that piezoelectric composition 131a is used.

Piezoelectric composition 131a is molded after the heat treatment step. Piezoelectric composition 131a can be molded by a known processing method such as machining or polishing, and, for example, the thickness of piezoelectric composition 131a is adjusted by such processing. The polishing is usually performed by mechanical polishing using an abrasive grain of diamond, SiC, alumina, or the like.

Piezoelectric element 130a can also be produced by a method including a step of disposing an electrode on piezoelectric composition 131a, and a step of applying an electric field to piezoelectric composition 131a.

At least two electrodes 132 are usually disposed on piezoelectric composition 131a. Electrodes 132 can be disposed by the same method as a usual method of disposing electrodes 132 on piezoelectric composition 131a. Examples of the material of electrodes 132 include gold, silver, platinum, palladium, nickel and copper. For example, a step of disposing electrodes 132 may be conducted by a method of baking silver or a silver-palladium paste, or a method of sputtering or vapor-depositing the electrode material. In the case of a silver paste, a baking treatment is preferably performed at, for example, about 400 to 700° C. for a short time. A buffer electrode of titanium or the like may also be disposed between each of electrodes 132 and piezoelectric composition 131a before disposing of electrodes 132 in order to enhance adhesiveness of piezoelectric composition 131a and each of electrodes 132.

The step of applying an electric field is a step of a polarization treatment of piezoelectric composition 131a (hereinafter, the step is also referred to as "polarization step"). While the polarization step can be performed in an oil bath at a high temperature, the step can also be performed in high vacuum or in a powder high in insulation, as another example. The polarization step may be performed before disposing of electrodes 132 on piezoelectric composition 131a, or may be performed after disposing of electrodes 132 on piezoelectric composition 131a. The electric field to be applied is not necessarily a direct current electric field, and may be of a high-frequency wave such as a rectangular wave, a saw-tooth wave or a burst wave, or may be superimposed on a direct current component.

The polarization step is usually performed in insulation oil after disposing of electrodes 132 on piezoelectric composition 131a. The treatment temperature is usually about several tens to 200° C. The intensity of the electric field to be applied is about 10 to 100 kV/cm. The step is preferably performed usually under conditions of a high temperature and a strong electric field. The treatment time is usually about 5 to 60 minutes.

In the polarization step, application of the electric field may be stopped, and piezoelectric composition 131a or piezoelectric element 130a may be taken out from the insulation oil, and then cooled. When the polarization treatment is more completely performed, field cooling with the electric field being applied in the insulation oil may also be performed. Such a polarization treatment can be performed to measure desired piezoelectric characteristics such as piezoelectric constant $d_{33}$ and to complete production of piezoelectric element 130a.

The method of producing piezoelectric element 130a may also further include other step depending on the intended mode of piezoelectric element 130a. For example, the production method may also further include a step of processing piezoelectric composition 131a into a desired shape. Piezoelectric composition 131a can be processed by a known processing method such as polishing or machining. While the processing of piezoelectric composition 131a is usually performed before production of electrodes 132, it may be performed after production of electrodes 132. For example, piezoelectric composition 131a can be processed into desired size and shape by cutting or machining before formation of electrodes 132, thereby producing piezoelectric element 130a.

Piezoelectric constant $d_{33}$ of piezoelectric composition 131a is preferably 200 pC/N or more, more preferably 400 pC/N or more from the viewpoint of an enhancement in performance of piezoelectric element 130a. Piezoelectric constant $d_{33}$ is increased by, for example, forming oriented ceramics or a single crystal oriented in a desired plane orientation from isotropic ceramics.

As described above, the polarization treatment can be reproducibly performed, and therefore piezoelectric element 130a having a predetermined piezoelectric constant can be obtained at a high productivity. Piezoelectric element 130a can be used in various actuators, inkjet heads, and sensors, and can be particularly suitably used in an ultrasound probe.

(Acoustic Matching Layer)

Acoustic matching layer 140 is a layer that allows the acoustic impedances of piezoelectric element 130a and a subject (when ultrasound probe 100a has an acoustic lens described below, such an acoustic lens) to be matched to suppress the reflection of an ultrasound at a boundary surface. Therefore, acoustic matching layer 140 has an acoustic impedance which is generally an intermediate impedance between the acoustic impedances of piezoelectric element 130a and the subject. Acoustic matching layer 140 is disposed on a surface of piezoelectric element 130a on the side facing the subject (front surface), for example, with one of the above electrodes being interposed.

Acoustic matching layer 140 may be a single-layer or a multi-layer, and is preferably a layered product made of a plurality of layers different in acoustic impedance, for example, preferably includes two or more layers, more preferably four or more layers from the viewpoint of adjustment of acoustic characteristics. The thickness of acoustic matching layer 140 is preferably $\lambda/4$, in which $\lambda$ means the wavelength of ultrasound.

Acoustic matching layer 140 can be formed from, for example, various materials. The acoustic impedance of acoustic matching layer 140 is preferably set so as to be stepwise or continuously closer to the acoustic impedance of the subject towards the acoustic lens, and can be adjusted by, for example, the type and the content of an additive to be added to the material.

Examples of the material of acoustic matching layer 140 include aluminum, an aluminum alloy (for example, Al—Mg alloy), a magnesium alloy, Macor glass, glass, fused quartz, copper graphite and a resin. Examples of the resin include polyethylene, polypropylene, polycarbonate, an ABS resin, an AAS resin, an AES resin, nylon such as nylon 6 and nylon 66, polyphenylene oxide, polyphenylene sulfide, polyphenylene ether, polyether ether ketone, polyamide-imide, polyethylene terephthalate, an epoxy resin, and a urethane resin.

Examples of the additive include zinc flower, titanium oxide, silica, alumina, colcothar, ferrite, tungsten oxide, ytterbium oxide, barium sulfate, tungsten, molybdenum, a glass fiber and a silicone particle.

For example, the surface portion of acoustic matching layer 140 is preferably formed from an epoxy resin and also preferably contains a silicone particle from the viewpoint of adjustment of the acoustic impedance of acoustic matching layer 140. As described below, when silicone as the material of the acoustic lens is dispersed in a substrate of acoustic matching layer 140 to thereby be present therein, the acoustic impedance of acoustic matching layer 140 can be close to that of the acoustic lens.

Respective layers in acoustic matching layer 140 are bonded by, for example, an adhesive (for example, epoxy-based adhesive) commonly used in the art.

(Flexible Printed Circuit)

FPC has a wiring to be connected to, for example, a pair of electrodes for piezoelectric composition 131a, the wiring having a pattern corresponding to piezoelectric element 130a. For example, without being particularly illustrated, FPC has a signal lead-out wiring serving as one electrode, and a ground lead-out wiring to be connected to other electrode. FPC may be a commercially available product as long as it has the above proper pattern.

Examples of the material of the electrodes include gold, platinum, silver, palladium, copper, aluminum, nickel, tin, and alloys including such metal elements. For example, the electrodes are each produced by first applying an underlying metal such as titanium or chromium by a sputtering method so that the thickness is 0.002 to 1.0 µm, and then applying the material, and further, if necessary, partially applying an insulating material, by a proper method such as a sputtering method or a vapor deposition method so that the thickness is 0.02 to 10 µm. The electrodes can also be each produced by applying a conductive paste obtained by mixing a fine metal powder and low-melting-point glass, by screen printing, a dipping method or a spraying method, to thereby form a layer of the conductive paste.

Ultrasound probe 100a may also further include other constituent component such as an acoustic lens that focuses an ultrasound beam.

The acoustic lens is formed from, for example, a flexible polymer material having an intermediate acoustic impedance between the acoustic impedances of the subject and acoustic matching layer 140. Examples of the polymer material include silicone-based rubber, butadiene-based rubber, polyurethane rubber, epichlorohydrin rubber, and ethylene-propylene copolymer rubber obtained by copolymerizing ethylene and propylene. In particular, the polymer material preferably includes silicone-based rubber and butadiene-based rubber.

Examples of the silicone-based rubber include silicone rubber and fluorine silicone rubber. In particular, the acoustic lens preferably includes silicone rubber. The silicone rubber refers to an organopolysiloxane which has a molecular skeleton including a Si—O bond and in which a plurality of organic groups are primarily bound to the Si atom. The silicone rubber usually includes methyl polysiloxane as a main component, and 90% or more of the entire organic groups are a methyl group. In the silicone rubber, at least a part of methyl groups of the methyl polysiloxane may be replaced with a hydrogen atom, a phenyl group, a vinyl group or an allyl group.

The silicone rubber can be obtained by, for example, kneading a curing agent (vulcanizing agent) such as benzoyl peroxide with organopolysiloxane high in the degree of polymerization, and curing the resultant by heating and vulcanizing. An organic or inorganic filler such as a silica or nylon powder, a vulcanization aid such as sulfur or zinc oxide, or the like may be further added depending on the purposes such as adjustment of the acoustic velocity and adjustment of the density in acoustic lens 170.

Examples of the butadiene-based rubber include butadiene rubber that is a homopolymer of butadiene, and copolymer rubber in which butadiene as a main component and a small amount of styrol or acrylonitrile are copolymerized. In particular, the acoustic lens preferably includes butadiene rubber. The butadiene rubber refers to synthetic rubber obtained by polymerization of butadiene having conjugated double bonds. The butadiene rubber can be obtained by homopolymerization of butadiene having conjugated double bonds at the 1,4-positions or the 1,2-positions. The butadiene rubber may be further vulcanized by sulfur.

An acoustic lens including silicone-based rubber and butadiene-based rubber can be produced by, for example, mixing silicone-based rubber and butadiene-based rubber, and curing the resulting mixture by vulcanizing. For example, the acoustic lens can be obtained by mixing silicone rubber and butadiene rubber in an appropriate ratio by a kneading roll, adding thereto a vulcanizing agent such as benzoyl peroxide, and crosslinking (curing) the resultant by heating and vulcanizing.

In the above case, zinc oxide is preferably further added as a vulcanization aid. Zinc oxide can promote vulcanization without any substantial loss in characteristics of the acoustic lens, resulting in a decrease in the vulcanizing time. Moreover, a colorant and/or other additive can be added as long as any of characteristics of the acoustic lens is not impaired. The mixing ratio of silicone-based rubber and butadiene-based rubber can be appropriately set. For example, the acoustic impedance of the acoustic lens is preferably set so that such an acoustic impedance is approximately that of the subject, the acoustic velocity in the acoustic lens is lower than that in the subject and the acoustic impedance of the acoustic lens is less attenuated. The mixing ratio of silicone-based rubber and butadiene-based rubber is preferably 1:1 from such viewpoints.

Ultrasound probe 100a may be, for example, a so-called array type ultrasound probe in which a plurality of piezoelectric elements 130a (channels) are disposed in parallel at a predetermined interval.

Ultrasound probe 100a may be subjected to waterproofing processing such as parylene coating so as to be usable in water or in a water-containing environment. For example, such waterproofing processing may be applied on the front surface of ultrasound probe 100a before bonding of the acoustic lens. The "parylene" is a registered trademark of Specialty Coating Systems, Inc.

Ultrasound probe 100a is suitably used in an ultrasound imaging apparatus. The ultrasound imaging apparatus can be configured in the same manner as in a known ultrasound imaging apparatus except for ultrasound probe 100a. The ultrasound imaging apparatus is suitable as, for example, an ultrasound diagnostic apparatus for medical use or a non-destructive ultrasound inspection apparatus.

Figure 3A:
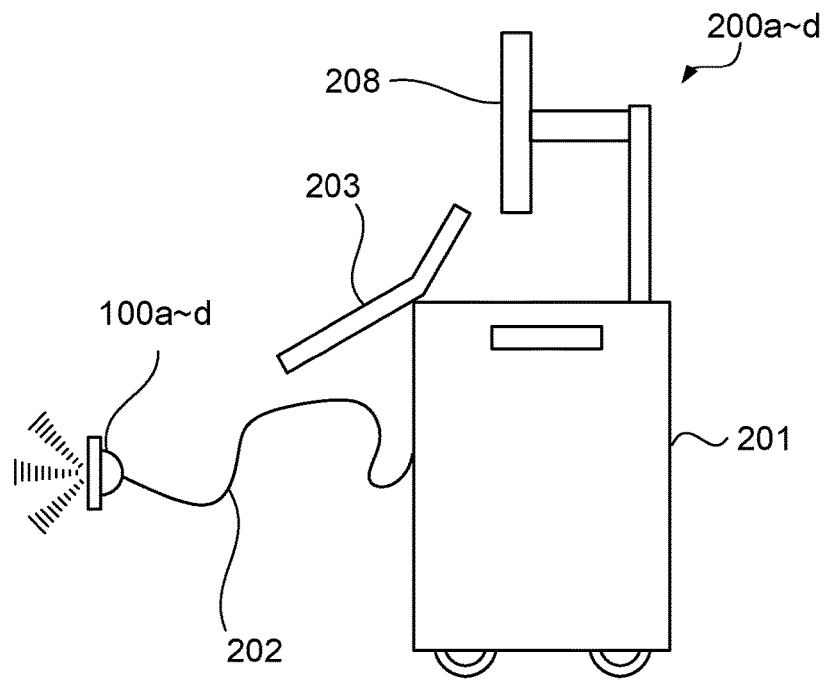
FIG. 3A illustrates a schematic view of one configuration example of an ultrasound imaging apparatus according to Embodiments of the present invention.
Figure 3B:
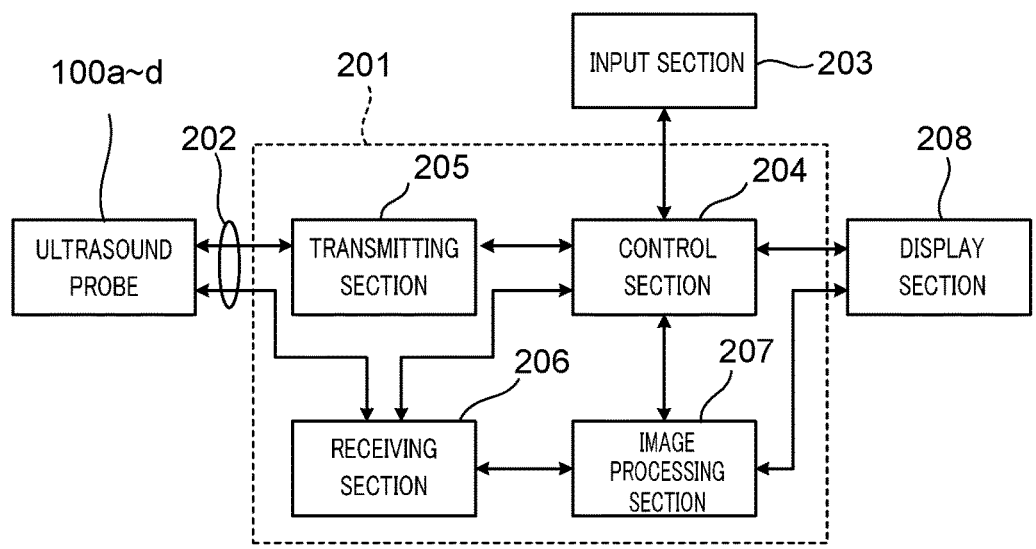
FIG. 3B illustrates a block diagram of one electric configuration example of the ultrasound imaging apparatus according to Embodiments of the present invention.

FIG. 3A illustrates a schematic view of one configuration example of ultrasound imaging apparatus 200a according to the present Embodiment, and FIG. 3B illustrates a block diagram of one electric configuration example of ultrasound imaging apparatus 200a.

Ultrasound imaging apparatus 200a includes, as illustrated in FIG. 3A, main body 201, ultrasound probe 100a connected to main body 201 via cable 202, and input section 203 and display section 208 disposed on main body 201.

Main body 201 includes, as illustrated in FIG. 3B, control section 204 connected to input section 203, transmitting section 205 and receiving section 206 each connected to control section 204 and cable 202, and image processing section 207 connected to each of receiving section 206 and control section 204. Control section 204 and image processing section 207 are each connected to display section 208.

Cable 202 connects ultrasound probe 100a and transmitting section 205, and connects ultrasound probe 100a and receiving section 206, to transmit a signal.

Input section 203 is an apparatus that allows data such as a command instructing the start of diagnosis or the like, and personal information of a subject to be input, and is, for example, an operation panel or a key board provided with a plurality of input switches.

Control section 204 is configured to include, for example, a microprocessor, a memory element, and a peripheral circuit thereof. Control section 204 is a circuit that controls ultrasound probe 100a, input section 203, transmitting section 205, receiving section 206, image processing section 207 and display section 208 depending on the respective functions, to thereby control the entire ultrasound diagnostic apparatus 200.

Transmitting section 205 transmits, for example, a signal from control section 204 to ultrasound probe 100a via cable 202.

Receiving section 206 receives, for example, a signal from ultrasound probe 100a, and outputs the signal to control section 204 or image processing section 207 via cable 202.

Image processing section 207 is, for example, a circuit that forms an image (ultrasound image) representing the internal state of a subject based on a signal received by receiving section 206 according to the control of control section 204. For example, image processing section 207 includes a Digital Signal Processor (DSP) that produces an ultrasound image of a subject, and a digital-analog conversion circuit (DAC circuit) that converts the signal processed in the DSP from a digital signal to an analog signal.

Display section 208 is, for example, an apparatus that displays an ultrasound image of a subject, the image being produced in image processing section 207 according to the control of control section 204. Display section 208 is, for example, a display apparatus such as a CRT display, a liquid crystal display (LCD), an organic EL display or a plasma display, or a printing apparatus such as a printer.

In ultrasound imaging apparatus 200a, control section 204 receives a signal from input section 203 and outputs to transmitting section 205 a signal that transmits ultrasound (first ultrasound signal) to a subject such as a living body, and control section 204 also allows receiving section 206 to receive an electrical signal corresponding to ultrasound (second ultrasound signal) from the subject based on the first ultrasound signal.

The electrical signal received by receiving section 206 is transmitted to image processing section 207, and processed into an image signal corresponding to the electrical signal.

The image signal is transmitted to display section 208, and an image corresponding to the image signal is displayed on display section 208. Display section 208 also displays an image and an operation (for example, displaying of a character, and transferring and enlarging of an image displayed) corresponding to information that is input from input section 203 and that is to be transmitted via control section 204, based on the information.

In ultrasound imaging apparatus 200a, an electrical signal as an ultrasound component is detected. Piezoelectric composition 131a has piezoelectric characteristics expressed by any coordinates included in a region formed by polyhedron 1. That is, piezoelectric composition 131a is sufficient in all of the bound relative permittivity, the coercive electric field and the effective electromechanical coupling coefficient. Therefore, ultrasound probe 100a including acoustic back layer 120 can achieve a high sensitivity to ultrasound, even when piezoelectric composition 131a has a small thickness. As a result, ultrasound imaging apparatus 200a can achieve precise and highly reliable measurement results due to a high spatial resolution. The reason for this is because piezoelectric composition 131a has piezoelectric characteristics expressed by any coordinates included in a region formed by polyhedron 1 to thereby improve electric impedance matching between a transmitting and receiving circuit and piezoelectric element 130a in ultrasound imaging apparatus 200a and also allow a sufficiently high coercive electric field to be ensured, and therefore even when piezoelectric composition 131a has a small thickness, depolarization and polarization degradation of piezoelectric composition 131a in voltage application can be inhibited from occurring.

Ultrasound imaging apparatus 200a is applied to an ultrasound diagnostic apparatus for medical use. Ultrasound imaging apparatus 200a can be applied to, in addition thereto, an apparatus that shows an ultrasound probing result by an image, a numerical value and the like, such as a fishfinder (sonar) and a flaw detector for non-destructive inspection.

As can be seen from the foregoing, the ultrasound probe is an ultrasound probe including a piezoelectric element including a piezoelectric composition and an electrode that applies a voltage to the piezoelectric composition, and an acoustic back layer acoustically coupled on the back surface of the piezoelectric element, in which the piezoelectric composition has piezoelectric characteristics expressed by any coordinates included in a region formed by a polyhedron having point A1 to point A18 shown below as vertexes in Cartesian coordinates ($k_{eff}$, $\varepsilon_{33}^S$, $E_c$) including variables $k_{eff}$, $\varepsilon_{33}^S$ and $E_c$. Therefore, the Embodiment can provide an ultrasound probe and an ultrasound imaging apparatus excellent in sensitivity to ultrasound even when a piezoelectric composition having a small thickness is adopted.

Point A1 (0.5, 2200, 18)
Point A2 (0.5, 1400, 18)
Point A3 (0.7, 600, 18)
Point A4 (0.9, 600, 18)
Point A5 (0.9, 2200, 18)
Point A6 (0.5, 2200, 15)
Point A7 (0.5, 1400, 15)
Point A8 (0.7, 600, 15)
Point A9 (0.9, 600, 15)
Point A10 (0.65, 2200, 10)
Point A11 (0.65, 1400, 10)
Point A12 (0.8, 600, 10)
Point A13 (0.9, 600, 10)
Point A14 (0.75, 2200, 7)
Point A15 (0.75, 1400, 7)
Point A16 (0.8, 1000, 7)
Point A17 (0.9, 1000, 7)
Point A18 (0.9, 2200, 7)

It is more effective that the center frequency of the transmitting and receiving band be 7 MHz or more from the viewpoint of realizing high-frequency driving.

It is much more effective that the piezoelectric composition satisfy the following expressions from the viewpoint of increasing the sensitivity to ultrasound.

$$k_{33} \geq 0.65$$

$$\varepsilon_{33}^S \geq 1000$$

$$E_c \geq 12$$

It is also much more effective that the piezoelectric composition include, as a main component, a composition represented by the following general formula (1) from the viewpoint of increasing the sensitivity to ultrasound.

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\} \quad (1)$$

In the general formula (1), A represents Ba or Sr, M1 represents Mg, or Mg and Zn, and the following expressions are satisfied.

$$0 \leq a2 \leq 0.1$$

$$a1+a2=1$$

$$x+y+z=1$$

$$0.1 \leq x \leq 0.375$$

$$0.5 \leq y/(y+z) \leq 0.64$$

It is much more effective that the piezoelectric composition include, as a main component, a composition represented by the following general formula (2) from the viewpoint of increasing the sensitivity to ultrasound.

$$x[(Pb_{a1}A_{a2})\{(M1_{1/3}Nb_{2/3})O_3\}]\text{-}y\{(Pb_{a1}A_{a2})TiO_3\}\text{-}z[R1\{(Pb_{a1}A_{a2})ZrO_3\}\text{---}R2(BiScO_3)] \quad (2)$$

In the general formula (2), A represents Ba or Sr, M1 represents Mg, or Mg and Zn, and the following expressions are satisfied.

$$0 \leq a2 \leq 0.1$$

$$a1+a2=1$$

$$x+y+z=1$$

$$0.1 \leq x \leq 0.25$$

$$0.5 \leq y/(y+z) \leq 0.64$$

$$0 < R2 \leq 0.25$$

It is more effective that the piezoelectric composition be ceramics oriented in a specific plane orientation from the viewpoint that high piezoelectric characteristics are exhibited as compared with a piezoelectric composition being isotropic ceramics, and it is also more effective that the piezoelectric composition be a single crystal having a specific plane orientation from the above viewpoint.

[Embodiment 2]

Ultrasound probe 100b according to Embodiment 2 includes piezoelectric element 130b in which a plurality of piezoelectric compositions 131 and a plurality of electrodes 132 are alternately stacked, as a structural feature.

Ultrasound probe 100b according to Embodiment 2 differs from ultrasound probe 100a according to Embodiment 1 in terms of only the configuration of piezoelectric element 130b. The same components as in ultrasound probe 100a according to Embodiment 1 are marked with the respective same symbols, and descriptions thereof are omitted. Any components different from those of ultrasound probe 100a are mainly described.

Figure 4:
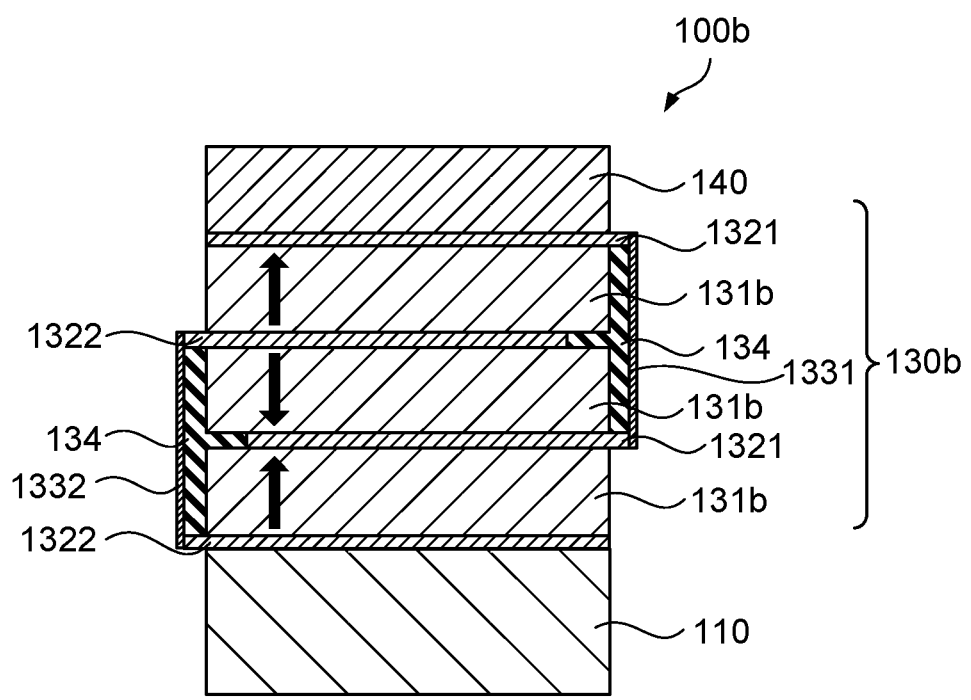
FIG. 4 illustrates a schematic cross-sectional view of one configuration example of an ultrasound probe according to Embodiment 2 of the present invention.

FIG. 4 illustrates a schematic cross-sectional view of one configuration example of ultrasound probe 100b according to Embodiment 2. Ultrasound probe 100b according to the present Embodiment includes back surface load material 110, piezoelectric element 130b, acoustic matching layer 140 and a flexible printed circuit (not illustrated).

(Piezoelectric Element)

Piezoelectric element 130b can convert an electrical signal to a mechanical vibration, and can also convert a mechanical vibration to an electrical signal. Thus, piezoelectric element 130b can transmit and receive ultrasound.

Piezoelectric element 130b is bonded to FPC by, for example, a conductive adhesive. The conductive adhesive is, for example, an adhesive containing a conductive material such as a silver powder, a copper powder, and a carbon fiber.

Piezoelectric element 130b according to the present Embodiment includes a plurality of piezoelectric compositions 131b, and electrode 132 that applies a voltage to each of the plurality of piezoelectric compositions 131b, and a layer of each of piezoelectric compositions 131b and electrode 132 are alternately stacked. The number of piezoelectric compositions 131b can be, if necessary, appropriately selected. In the present Embodiment, three layers of piezoelectric compositions 131b and four layers of electrodes 132 (two electrodes 1321 and two electrodes 1322) are alternately stacked.

Piezoelectric element 130b includes, as illustrated in FIG. 4, a plurality of piezoelectric compositions 131b, a plurality of electrodes 1321 and 1322 each disposed between a plurality of piezoelectric compositions 131b, lead-out electrodes 1331 and 1332 that each mutually connect electrodes 1321 and mutually connect electrodes 1322, respectively, and each insulator 134 that insulates each electrode 1321 and each electrode 1322.

Piezoelectric compositions 131b may be any as long as they have piezoelectricity, and may be each ceramics, oriented ceramics, an inorganic/organic composite, or a single crystal.

Piezoelectric compositions 131b are each disposed so that polarization directions are opposite to each other between adjacent piezoelectric compositions 131b in the layering direction. Each arrow in FIG. 4 indicates the polarization direction of each piezoelectric composition 131b. Electrodes 1321 are protruded onto one end of piezoelectric compositions 131b in the planar direction, and electrodes 1322 are protruded onto other end thereof in the planar direction. Electrodes 1321 and 1322 are connected to lead-out electrodes 1331 and 1332 at ends protruded, respectively. Insulator 134 is filled in a space between other ends of electrodes 1321 and lead-out electrode 1332, and a space between electrodes 1322 and lead-out electrode 1331, thereby preventing an electrode not connected to a lead-out electrode from being connected to the lead-out electrode.

An ultrasound probe (ultrasound probe 100b) usually allows piezoelectric element 130b to be operated at an impedance of about 50Ω. Piezoelectric element 130b having a multi-layered structure can be produced by, for example, layering and pressure-bonding green sheets of piezoelectric compositions 131b and electrodes 132, and subjecting the resultant to a known production method including respective steps of debindering, sintering, cutting, electrode-mounting, leading out by a lead wire, and the like.

Ultrasound probe 100b may be, for example, a so-called array type ultrasound probe in which a plurality of piezoelectric elements 130b (channels) are disposed in parallel at a predetermined interval. The ultrasound probe is generally easily decreased in the area of a portion thereof to be irradiated with ultrasound, and therefore is easily decreased in the area of a portion thereof on which the piezoelectric elements are arrayed. Therefore, piezoelectric element 130b is preferably piezoelectric element 130b having a multi-layered structure in which layers of a plurality of piezoelectric compositions 131b and a plurality of electrodes 132 are alternately stacked, from the viewpoint that transmitting and receiving impedance matching of ultrasound is more easily conducted. Piezoelectric element 130b having a multi-layered structure is preferable from the viewpoint that the impedance in piezoelectric element 130b is reduced to allow transmitting and receiving of ultrasound to be efficiently performed.

Figure 5:
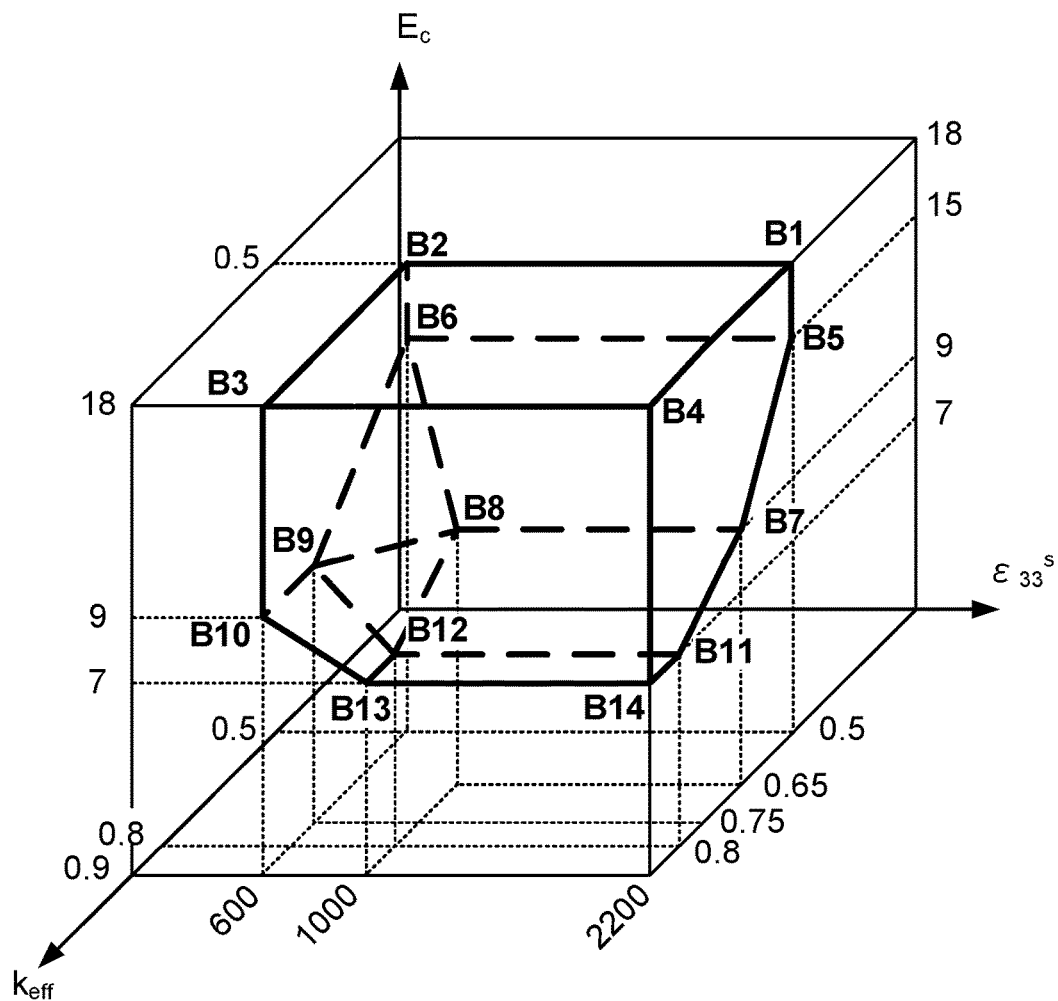
FIG. 5 illustrates a schematic view illustrating piezoelectric characteristics of a piezoelectric composition according to Embodiment 2 of the present invention.
Figure 6:
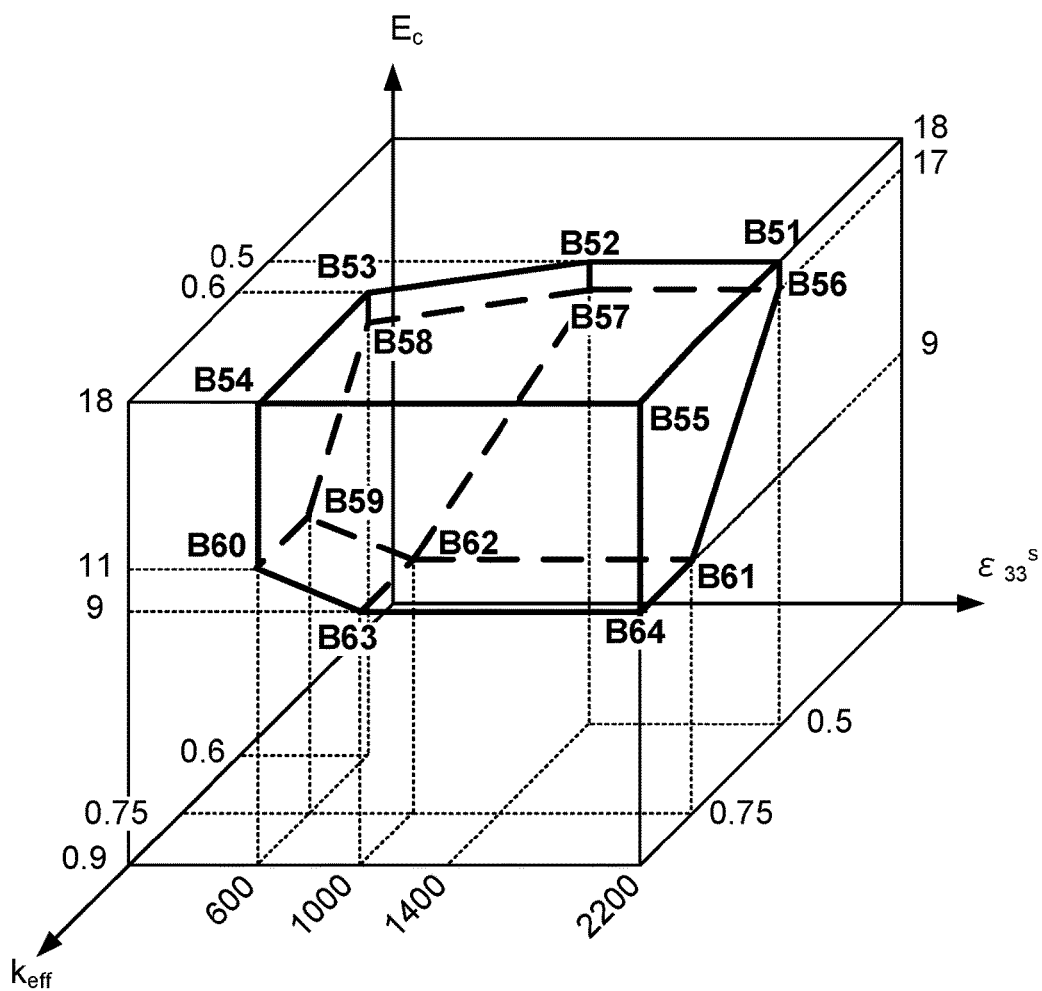
FIG. 6 illustrates a schematic view illustrating piezoelectric characteristics of a piezoelectric composition according to Embodiment 2 of the present invention.

FIG. 5 and FIG. 6 each illustrate a schematic view illustrating piezoelectric characteristics of each piezoelectric composition 131b according to Embodiment 2. Each piezoelectric composition 131b, as illustrated in FIG. 5, has piezoelectric characteristics expressed by any coordinates included in a region formed by polyhedron 2 having point B1 to point B14 shown below as vertexes in Cartesian coordinates ($k_{eff}$, $\varepsilon_{33}^S$, $E_c$) including variables $k_{eff}$, $\varepsilon_{33}^S$ and $E_c$ when the effective electromechanical coupling coefficient, the bound relative permittivity and the coercive electric field thereof are defined as $k_{eff}$, $\varepsilon_{33}^S$ and $E_c$ (kV/cm), respectively:

Point B1 (0.5, 2200, 18)
Point B2 (0.5, 600, 18)
Point B3 (0.9, 600, 18)
Point B4 (0.9, 2200, 18)
Point B5 (0.5, 2200, 15)
Point B6 (0.5, 600, 15)
Point B7 (0.65, 2200, 9)
Point B8 (0.65, 1000, 9)
Point B9 (0.75, 600, 9)
Point B10 (0.9, 600, 9)
Point B11 (0.8, 2200, 7)
Point B12 (0.8, 1000, 7)
Point B13 (0.9, 1000, 7)
Point B14 (0.9, 2200, 7)

If each piezoelectric composition 131b is too low in at least one of $k_{eff}$, $\varepsilon_{33}^S$ and $E_c$ to have piezoelectric characteristics expressed by any coordinates included in a region formed by polyhedron 2, a sufficient sensitivity to ultrasound is not achieved. Each piezoelectric composition 131b which is too high in at least one of $k_{eff}$, $\varepsilon_{33}^S$ and $E_c$ to have piezoelectric characteristics expressed by any coordinates included in a region formed by polyhedron 2 is not preferable because of being difficult to actually produce.

Each piezoelectric composition 131b, as illustrated in FIG. 6, preferably has piezoelectric characteristics expressed by any coordinates included in a region formed by polyhedron 2' having point B51 to point B64 shown below as vertexes from the viewpoint of realizing a high sensitivity to ultrasound.

Point B51 (0.5, 2200, 18)
Point B52 (0.5, 1400, 18)
Point B53 (0.6, 600, 18)
Point B54 (0.9, 600, 18)
Point B55 (0.9, 2200, 18)
Point B56 (0.5, 2200, 17)
Point B57 (0.5, 1400, 17)
Point B58 (0.6, 600, 17)
Point B59 (0.75, 600, 11)
Point B60 (0.9, 600, 11)
Point B61 (0.75, 2200, 9)
Point B62 (0.75, 1000, 9)
Point B63 (0.9, 1000, 9)
Point B64 (0.9, 2200, 9)

The thickness of each piezoelectric composition 131b can be appropriately set depending on the center frequency of ultrasound, the frequency constant of each piezoelectric composition 131b, the acoustic design, and the like. The thickness of each piezoelectric composition 131b is preferably small from the viewpoint of realizing a high center frequency. For example, the thickness of each piezoelectric composition 131b is preferably in the range from 0.02 to 1 mm, more preferably in the range from 0.03 to 0.5 mm. When the center frequency is 7 MHz, the thickness of each piezoelectric composition 131b is, for example, in the range from 0.05 to 0.2 mm.

Each piezoelectric composition 131b also satisfies the following expressions from the viewpoint of realizing a high sensitivity to ultrasound:

$$k_{33} \geq 0.65$$

$$\varepsilon_{33}^S \geq 1000$$

$$E_c \geq 12.$$

The composition of each piezoelectric composition 131b can be appropriately changed as long as at least one of the effects of the present Embodiment is obtained. Examples of the composition of each piezoelectric composition 131b are the same as those of piezoelectric composition 131a according to Embodiment 1.

FIG. 3A schematically illustrates one configuration example of ultrasound imaging apparatus 200b according to the present Embodiment, and FIG. 3B illustrates a block diagram of one electric configuration example of ultrasound imaging apparatus 200b.

Ultrasound probe 100b is also suitably used in an ultrasound imaging apparatus. Ultrasound imaging apparatus 200b can be configured in the same manner as in a known ultrasound imaging apparatus except for ultrasound probe 100b. The ultrasound imaging apparatus is suitable as, for example, an ultrasound diagnostic apparatus for medical use or a non-destructive ultrasound inspection apparatus.

Also in ultrasound imaging apparatus 200b, an electrical signal as an ultrasound component is detected as in ultrasound imaging apparatus 200a according to Embodiment 1. Each piezoelectric composition 131b has piezoelectric characteristics expressed by any coordinates included in a region formed by polyhedron 2 or polyhedron 2'. That is, each piezoelectric composition 131b is sufficient in all of the bound relative permittivity, the coercive electric field and the effective electromechanical coupling coefficient. Thus, ultrasound probe 100b including piezoelectric element 130b in which a plurality of piezoelectric compositions 131b and a plurality of electrodes 132 are alternately stacked can achieve a high sensitivity to ultrasound high in center frequency. As a result, ultrasound imaging apparatus 200b can achieve precise and high-reliable measurement results due to a high spatial resolution. The reason for this is because each piezoelectric composition 131b has piezoelectric characteristics expressed by any coordinates included in a region formed by polyhedron 2 or polyhedron 2' to thereby enable a signal received by ultrasound imaging apparatus 200b to be efficiently transmitted to piezoelectric element 130b and also allow a sufficiently high coercive electric field to be ensured, and therefore even when the thickness of each piezoelectric composition 131b is low, depolarization and polarization degradation of each piezoelectric composition 131b in voltage application can be inhibited from occurring.

As can be seen from the foregoing, the ultrasound probe is an ultrasound probe including a piezoelectric element including a plurality of piezoelectric compositions, and an electrode that applies a voltage to each of the plurality of piezoelectric compositions, respectively, and a layer of each of the piezoelectric compositions and the electrode are alternately stacked, in which each of the piezoelectric compositions has piezoelectric characteristics expressed by any coordinates included in a region formed by a polyhedron having point B1 to point B14 shown below as vertexes in Cartesian coordinates ($k_{eff}$, $\varepsilon_{33}^S$, $E_c$) including variables $k_{eff}$, $\varepsilon_{33}^S$ and $E_c$. Therefore, the Embodiment can provide an ultrasound probe and an ultrasound imaging apparatus excellent in sensitivity to ultrasound, even when a piezoelectric compositions having a small thickness is adopted.

Point B1 (0.5, 2200, 18)
Point B2 (0.5, 600, 18)
Point B3 (0.9, 600, 18)
Point B4 (0.9, 2200, 18)
Point B5 (0.5, 2200, 15)
Point B6 (0.5, 600, 15)
Point B7 (0.65, 2200, 9)
Point B8 (0.65, 1000, 9)
Point B9 (0.75, 600, 9)
Point B10 (0.9, 600, 9)
Point B11 (0.8, 2200, 7)
Point B12 (0.8, 1000, 7)
Point B13 (0.9, 1000, 7)
Point B14 (0.9, 2200, 7)

It is thus much more effective that the piezoelectric element in the ultrasound probe be configured so as to allow the plurality of the piezoelectric compositions and the plurality of electrodes to be alternately stacked, from the viewpoint that the impedance in transmitting and receiving of ultrasound in the piezoelectric element is reduced.

It is also much more effective that the piezoelectric element have piezoelectric characteristics expressed by any coordinates included in a region formed by a polyhedron having point B51 to point B64 shown below as vertexes from the viewpoint that a high sensitivity to ultrasound high in center frequency is achieved.

Point B51 (0.5, 2200, 18)
Point B52 (0.5, 1400, 18)
Point B53 (0.6, 600, 18)
Point B54 (0.9, 600, 18)
Point B55 (0.9, 2200, 18)
Point B56 (0.5, 2200, 17)

Point B57 (0.5, 1400, 17)
Point B58 (0.6, 600, 17)
Point B59 (0.75, 600, 11)
Point B60 (0.9, 600, 11)
Point B61 (0.75, 2200, 9)
Point B62 (0.75, 1000, 9)
Point B63 (0.9, 1000, 9)
Point B64 (0.9, 2200, 9)

[Embodiment 3]

Ultrasound probe 100c according to Embodiment 3 includes piezoelectric element 130c including a single-layer piezoelectric composition and no acoustic back layer, as a structural feature.

Ultrasound probe 100c according to Embodiment 3 differs from ultrasound probe 100a according to Embodiment 1 in that piezoelectric element 130c includes no acoustic back layer. The same components as in ultrasound probe 100a according to Embodiment 1 are marked with the respective same symbols, and descriptions thereof are omitted.

Figure 7:
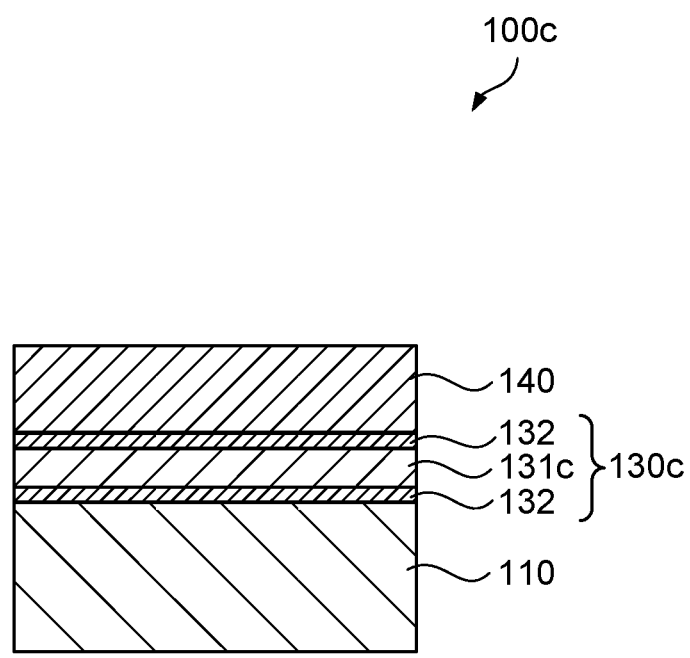
FIG. 7 illustrates a schematic cross-sectional view of one configuration example of an ultrasound probe according to Embodiment 3 of the present invention.

FIG. 7 illustrates a schematic cross-sectional view of one configuration example of ultrasound probe 100c according to Embodiment 3. Ultrasound probe 100c according to the present Embodiment includes back surface load material 110, piezoelectric element 130c, acoustic matching layer 140, and a flexible printed circuit (not illustrated). As described above, ultrasound probe 100c according to the present Embodiment includes no acoustic back layer to be acoustically coupled on the back surface of the piezoelectric element.

(Piezoelectric Element)

Piezoelectric element 130c can convert an electrical signal to a mechanical vibration, and can also convert a mechanical vibration to an electrical signal. Thus, piezoelectric element 130c can transmit and receive ultrasound.

Piezoelectric element 130c is bonded to FPC by, for example, a conductive adhesive. The conductive adhesive is, for example, an adhesive containing a conductive material such as a silver powder, a copper powder and a carbon fiber.

Piezoelectric element 130c according to the present Embodiment includes single-layer piezoelectric composition 131c, and electrode 132 that applies a voltage to piezoelectric composition 131c.

Piezoelectric composition 131c may be any as long as it has piezoelectricity, and may be ceramics, oriented ceramics, an inorganic/organic composite, or a single crystal.

Figure 8:
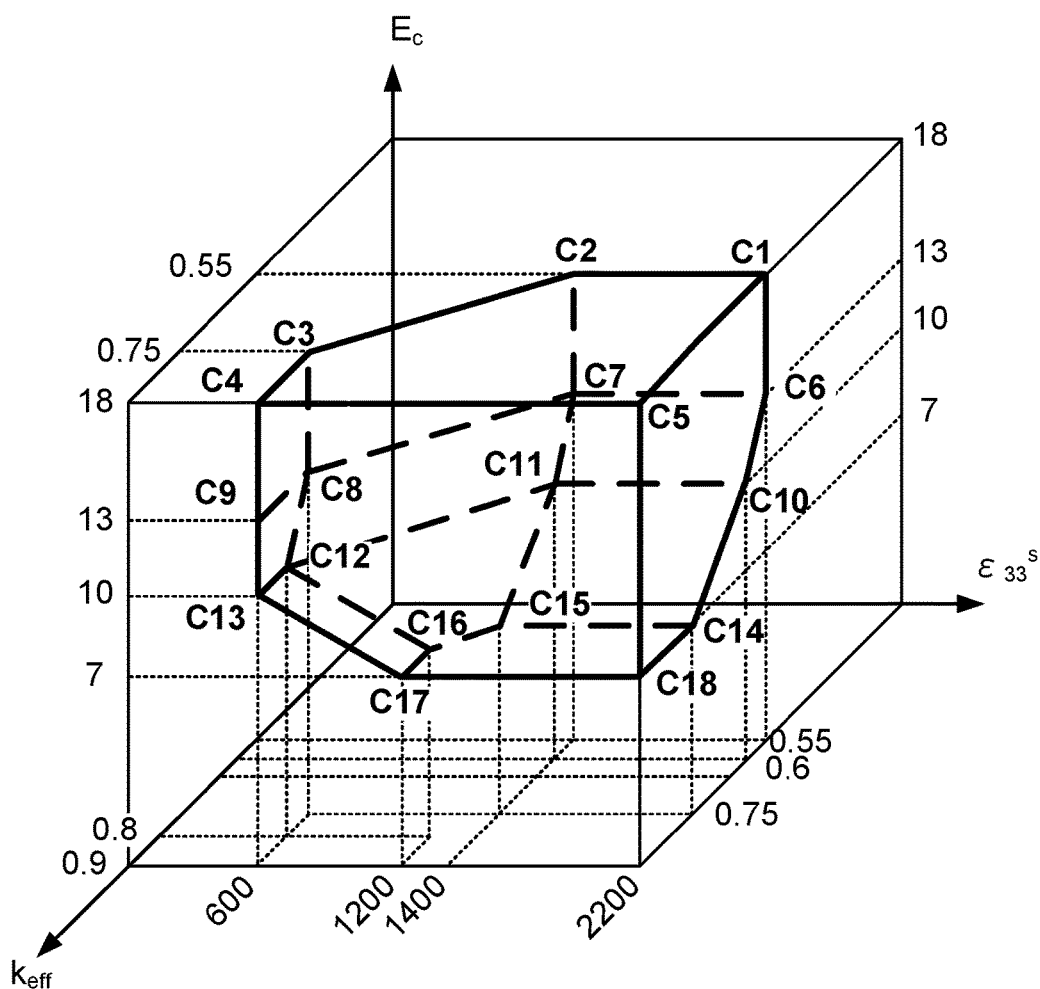
FIG. 8 illustrates a schematic view illustrating piezoelectric characteristics of a piezoelectric composition according to Embodiment 3 of the present invention.

FIG. 8 schematically illustrates piezoelectric characteristics of the piezoelectric composition according to Embodiment 3. Piezoelectric composition 131c, as illustrated in FIG. 8, has piezoelectric characteristics expressed by any coordinates included in a region formed by polyhedron 3 having point C1 to point C18 shown below as vertexes in Cartesian coordinates ($k_{eff}$, $\varepsilon_{33}^S$, a) including variables $k_{eff}$, $\varepsilon_{33}^S$ and E.

Point C1 (0.55, 2200, 18)
Point C2 (0.55, 1400, 18)
Point C3 (0.75, 600, 18)
Point C4 (0.9, 600, 18)
Point C5 (0.9, 2200, 18)
Point C6 (0.55, 2200, 13)
Point C7 (0.55, 1400, 13)
Point C8 (0.75, 600, 13)
Point C9 (0.9, 600, 13)
Point C10 (0.6, 2200, 10)
Point C11 (0.6, 1400, 10)
Point C12 (0.8, 600, 10)
Point C13 (0.9, 600, 10)
Point C14 (0.75, 2200, 7)
Point C15 (0.75, 1400, 7)
Point C16 (0.8, 1200, 7)
Point C17 (0.9, 1200, 7)
Point C18 (0.9, 2200, 7)

If piezoelectric composition 131c is too low in at least one of $k_{eff}$, $\varepsilon_{33}^S$ and a to have piezoelectric characteristics expressed by any coordinates included in a region formed by polyhedron 3, a sufficient sensitivity to ultrasound is not achieved. On the other hand, piezoelectric composition 131c which is too high in at least one of $k_{eff}$, $\varepsilon_{33}^S$ and a to have piezoelectric characteristics expressed by any coordinates included in a region formed by polyhedron 3 is not preferable because of being difficult to actually produce.

The thickness of piezoelectric composition 131c can be appropriately set depending on the center frequency of ultrasound, the frequency constant of piezoelectric composition 131c, the acoustic design, and the like. The thickness of piezoelectric composition 131c is preferably small from the viewpoint of realizing a high center frequency. For example, the thickness of piezoelectric composition 131c is preferably in the range from 0.02 to 1 mm, more preferably in the range from 0.03 to 0.5 mm. When the center frequency is 15 MHz, the thickness of piezoelectric composition 131c is, for example, in the range from 0.04 to 0.2 mm.

Piezoelectric composition 131c also satisfies the following expressions from the viewpoint of realizing a high sensitivity to ultrasound.

$$k_{33} \geq 0.65$$

$$\varepsilon_{33}^S \geq 1000$$

$$E_c \geq 12$$

The composition of piezoelectric composition 131c can be appropriately changed as long as at least one of the effects of the present Embodiment is obtained. Examples of the composition of piezoelectric composition 131c are the same as those of piezoelectric composition 131a according to Embodiment 1.

FIG. 3A schematically illustrates one configuration example of ultrasound imaging apparatus 200c according to the present Embodiment, and FIG. 3B illustrates a block diagram illustrating one electric configuration example of ultrasound imaging apparatus 200c.

Ultrasound probe 100c is also suitably used in an ultrasound imaging apparatus. Ultrasound imaging apparatus 200c can be configured in the same manner as in a known ultrasound imaging apparatus except for ultrasound probe 100c. The ultrasound imaging apparatus is suitable as, for example, an ultrasound diagnostic apparatus for medical use or a non-destructive ultrasound inspection apparatus.

Ultrasound probe 100c may also be, for example, a so-called array type ultrasound probe in which a plurality of piezoelectric elements 130c (channels) are disposed in parallel at a predetermined interval.

Also in ultrasound imaging apparatus 200c, an electrical signal as an ultrasound component is detected as in ultrasound imaging apparatus 200a according to Embodiment 1. Each piezoelectric composition 131c has piezoelectric characteristics expressed by any coordinates included in a region formed by polyhedron 3. That is, each piezoelectric composition 131c is sufficient in all of the bound relative permittivity, the coercive electric field and the effective electromechanical coupling coefficient. Therefore, ultrasound probe 100c including single-layer piezoelectric composition 131c and no acoustic back layer can achieve a high sensitivity to ultrasound high in center frequency. As a result, ultrasound imaging apparatus 200c can achieve precise and highly reliable measurement results due to a high spatial resolution. The reason for this is because each piezoelectric composition 131c has piezoelectric characteristics expressed by any coordinates included in a region formed by polyhedron 3 to thereby enable a signal received by ultrasound imaging apparatus 200c to be efficiently transmitted to piezoelectric element 130c and also allow a sufficiently high coercive electric field to be ensured, and therefore even when the thickness of each piezoelectric composition 131c is small, depolarization and polarization degradation of each piezoelectric composition 131c in voltage application can be inhibited from occurring.

As can be seen from the foregoing, the ultrasound probe is an ultrasound probe including a piezoelectric element including a single-layer piezoelectric composition and an electrode that applies a voltage to the piezoelectric composition, and no acoustic back layer to be acoustically coupled to the piezoelectric element on the back surface of the piezoelectric element, in which the piezoelectric composition has piezoelectric characteristics expressed by any coordinates included in a region formed by a polyhedron having point C1 to point C18 shown below as vertexes in Cartesian coordinates ($k_{eff}$, $\varepsilon_{33}^S$, $E_c$) including variables $k_{eff}$, $\varepsilon_{33}^S$ and $E_c$. Therefore, the Embodiment can provide an ultrasound probe and an ultrasound imaging apparatus excellent in sensitivity to ultrasound, even when a piezoelectric composition having a small thickness is adopted.

Point C1 (0.55, 2200, 18)
Point C2 (0.55, 1400, 18)
Point C3 (0.75, 600, 18)
Point C4 (0.9, 600, 18)
Point C5 (0.9, 2200, 18)
Point C6 (0.55, 2200, 13)
Point C7 (0.55, 1400, 13)
Point C8 (0.75, 600, 13)
Point C9 (0.9, 600, 13)
Point C10 (0.6, 2200, 10)
Point C11 (0.6, 1400, 10)
Point C12 (0.8, 600, 10)
Point C13 (0.9, 600, 10)
Point C14 (0.75, 2200, 7)
Point C15 (0.75, 1400, 7)
Point C16 (0.8, 1200, 7)
Point C17 (0.9, 1200, 7)
Point C18 (0.9, 2200, 7)

It is thus much more effective that the piezoelectric element in the ultrasound probe be configured so as to allow the plurality of the piezoelectric compositions and the plurality of electrodes to be alternately stacked, from the viewpoint that the impedance in transmitting and receiving of ultrasound in the piezoelectric element is reduced.

It is also much more effective that the ultrasound probe include the piezoelectric element including a single-layer piezoelectric composition and the electrode that applies a voltage to the piezoelectric composition, and no acoustic back layer to be acoustically coupled on the back surface of the piezoelectric element, from the viewpoint of simplifying the configuration of the ultrasound probe.

[Embodiment 4]

An ultrasound probe according to Embodiment 4 includes a characteristic piezoelectric composition in a piezoelectric element. The ultrasound probe according to Embodiment 4 may be any ultrasound probe of ultrasound probe 100a according to Embodiment 1, ultrasound probe 100b according to Embodiment 2 and ultrasound probe 100c according to Embodiment 3. In Embodiment 4 below, ultrasound probe 100d having the same configuration as in ultrasound probe 100a according to Embodiment 1 is described, and descriptions of the same components as in ultrasound probe 100a are omitted.

The piezoelectric composition may be any as long as it has piezoelectricity, and may be ceramics, oriented ceramics, an inorganic/organic composite, or a single crystal.

The piezoelectric composition of the ultrasound probe according to the present Embodiment satisfies the following expressions when the electromechanical coupling coefficient, the bound relative permittivity and the coercive electric field thereof are defined as $k_{33}$, $\varepsilon_{33}^S$ and $E_c$ (kV/cm), respectively:

$k_{33} \geq 0.65$ $\varepsilon_{33}^S \geq 1000$ $E_c \geq 12$.

$k_{33}$ and the measurement method thereof, $\varepsilon_{33}^S$ and the measurement method thereof, and $E_c$ and the measurement method thereof are the same as those in Embodiment 1, and therefore descriptions thereof are omitted. The adjustment methods of $k_{33}$, $\varepsilon_{33}^S$ and $E_c$ are described below.

"$k_{33}$" can be adjusted by the composition of the piezoelectric composition, the relative density to the theoretical density (when the piezoelectric composition is ceramics), the crystal orientation of the piezoelectric composition, and the like. As the composition of the piezoelectric composition is closer to the morphotropic phase boundary (MPB), "$k_{33}$" tends to be higher. In addition, as the relative density of the piezoelectric composition is higher, "$k_{33}$" tends to be higher.

"$\varepsilon_{33}^S$" can be adjusted by the composition of the piezoelectric composition. For example, as the content of $Mg_{1/3}Nb_{2/3}$ in the piezoelectric composition is higher, "$\varepsilon_{33}^S$" tends to be higher. In addition, as the composition of the piezoelectric composition is closer to the morphotropic phase boundary (MPB), "$\varepsilon_{33}^S$" tends to be higher.

"$E_c$" can be adjusted by the composition of the piezoelectric composition, the composition of impurities, and the like. When $E_c$ is adjusted by impurities, $\varepsilon_{33}^S$ tends to be lower as $E_c$ is higher, and when $\varepsilon_{33}^S$ is too low, a piezoelectric composition usable in an ultrasound probe is difficult to produce. $E_c$ is preferably adjusted in view of such a viewpoint. For example, the present inventors have first found that a PMN-PZT-based material, in particular $BiScO_3$, can be contained to thereby not only increase $E_c$ with $\varepsilon_{33}^S$ being kept, but also increase piezoelectric characteristics ($k_{33}$ and $d_{33}$) in a direction parallel with the polarization direction.

The thickness of the piezoelectric composition can be appropriately set depending on the center frequency of ultrasound, the frequency constant of the piezoelectric composition, the acoustic design, and the like. The thickness of the piezoelectric composition is preferably small from the viewpoint of realizing a high center frequency. For example, the thickness of the piezoelectric composition is preferably in the range from 0.02 to 1 mm, more preferably in the range from 0.03 to 0.5 mm, further preferably in the range from 0.04 to 0.2 mm. When the center frequency is 10 MHz, the thickness of the piezoelectric composition is, for example, in the range from 0.04 to 0.2 mm.

The composition of the piezoelectric composition can be appropriately changed as long as at least one of the effects of the present Embodiment is obtained. The piezoelectric composition may be produced by the above-mentioned production method, or may be a ready-made product. The piezoelectric composition preferably includes, as a main component, a composition represented by the following general formula (1), more preferably includes, as a main component, a composition represented by the following general formula (2), from the viewpoint of realizing a high sensitivity to ultrasound.

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\} \quad (1)$$

In the general formula (1), A represents Ba or Sr, M1 represents Mg, or Mg and Zn, and the following expressions are satisfied. When M1 represents Mg and Zn, the ratio of Mg and Zn is not particularly limited, and is, for example, 10:0 to 5:5.

$$0 \le a2 \le 0.1$$

$$a1+a2=1$$

$$x+y+z=1$$

$$0.1 \le x \le 0.375$$

$$0.5 \le y/(y+z) \le 0.64$$

$$x[(Pb_{a1}A_{a2})\{(M1_{1/3}Nb_{2/3})O_3\}]\text{-}y\{(Pb_{a1}A_{a2})TiO_3\}\text{-}z[R1\{(Pb_{a1}A_{a2})ZrO_3\}\text{---}R2(BiScO_3)] \quad (2)$$

In the general formula (2), A represents Ba or Sr, M1 represents Mg, or Mg and Zn, and the following expressions are satisfied. When M1 represents Mg and Zn, the ratio of Mg and Zn is not particularly limited, and is, for example, 10:0 to 5:5.

$$0 \le a2 \le 0.1$$

$$a1+a2=1$$

$$x+y+z=1$$

$$0.1 \le x \le 0.25$$

$$0.5 \le y/(y+z) \le 0.64$$

$$0 < R2 \le 0.25$$

In the general formulae (1) and (2), the values of a1, a2, x, y, z and R2 can be appropriately set as long as at least one of the effects of the present Embodiment is obtained. If barium (Ba) or strontium (Sr) is excessively added to the piezoelectric composition, $k_{33}$ may be excessively lower, and therefore a2 is preferably 0.1 or less. The present inventors have also first found that the inclusion of $BiScO_3$ in the piezoelectric composition is effective for increasing $E_c$, $k_{33}$ and piezoelectric constant $d_{33}$ with $\varepsilon_{33}^S$ being kept.

While the piezoelectric composition includes, as a main component, any composition represented by the general formulae (1) and (2), such any composition may vary in terms of the contents of Pb and Bi evaporated, as long as a perovskite structure is stably kept. The piezoelectric composition may also contain other accessory component, as in the piezoelectric composition according to Embodiment 1.

Each microcrystal of the piezoelectric composition may be ceramics oriented in a specific plane orientation (so-called oriented ceramics) or may be a single crystal having a specific plane orientation. The specific plane orientation, while it may be in any orientation, is preferably (111), (110) or (001) in terms of a pseudocubic crystal from the viewpoint of more enhancing piezoelectricity. The orientation method of ceramics and the contents of various elements in the piezoelectric composition are the same as those in Embodiment 1, and therefore descriptions thereof are omitted.

Examples of the method of producing the piezoelectric composition are also the same as the method of producing piezoelectric composition 131a according to Embodiment 1, and therefore description thereof are omitted.

Figure 9:
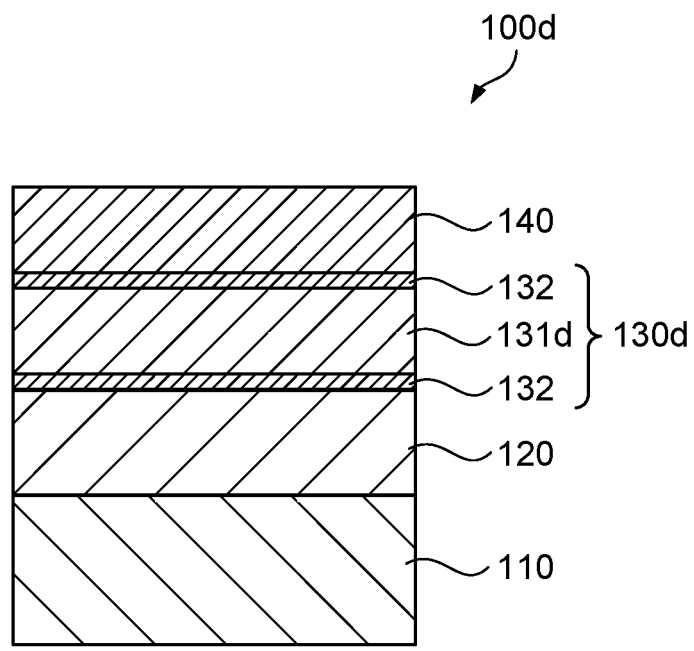
FIG. 9 illustrates a schematic cross-sectional view of one configuration example of an ultrasound probe according to Embodiment 4 of the present invention.

FIG. 9 illustrates a schematic cross-sectional view illustrating a configuration of ultrasound probe 100d according to Embodiment 4. Ultrasound probe 100d according to the present Embodiment includes back surface load material 110, acoustic back layer 120, piezoelectric element 130d, acoustic matching layer 140, and a flexible printed circuit (FPC, not illustrated). Piezoelectric element 130d according to the present Embodiment includes single-layer piezoelectric composition 131d, and electrode 132 that applies a voltage to piezoelectric composition 131d. In the present Embodiment, two electrodes 132 are disposed on both surfaces of piezoelectric composition 131d so as to be opposite to each other with piezoelectric composition 131d interposed therebetween.

FIG. 3A illustrates a schematic view of one configuration example of ultrasound imaging apparatus 200d according to the present Embodiment, and FIG. 3B illustrates a block diagram of one electric configuration example of ultrasound imaging apparatus 200d.

Ultrasound imaging apparatus 200d includes, as illustrated in FIG. 3A, main body 201, ultrasound probe 100d connected to main body 201 via cable 202, and input section 203 and display section 208 disposed on main body 201.

Also in ultrasound imaging apparatus 200d, an electrical signal as an ultrasound component is detected as in ultrasound imaging apparatus 200a according to Embodiment 1. Ultrasound probe 100d of ultrasound imaging apparatus 200d includes piezoelectric composition 131d. Piezoelectric composition 131b is sufficient in all of the bound relative permittivity, the coercive electric field and the effective electromechanical coupling coefficient. Therefore, ultrasound probe 100d including acoustic back layer 120 can achieve a high sensitivity to ultrasound, even when piezoelectric composition 131d has a small thickness. As a result, ultrasound imaging apparatus 200d can achieve precise and highly reliable measurement results due to a high spatial resolution. The reason for this is because ultrasound probe 100d includes piezoelectric composition 131d to thereby improve electric impedance matching of piezoelectric element 130d and also allow a sufficiently high coercive electric field to be ensured, and therefore even when piezoelectric composition 131d has a small thickness, depolarization and polarization degradation of piezoelectric composition 131d in voltage application can be inhibited from occurring.

As can be seen from the foregoing, the piezoelectric element includes a piezoelectric composition including, as a main component, a composition represented by the following general formula, and an electrode that applies a voltage to the piezoelectric composition, in which the piezoelectric composition satisfies the following expressions (1) to (3) when the electromechanical coupling coefficient, the bound relative permittivity and the coercive electric field thereof are defined as $k_{33}$, $\varepsilon_{33}^S$ and $E_c$ (kV/cm), respectively. Therefore, the Embodiment can provide a piezoelectric element, an ultrasound probe and an ultrasound imaging apparatus excellent in sensitivity to ultrasound even when a piezoelectric composition having a small thickness is adopted.

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\}$$

in which A represents Ba or Sr, M1 represents Mg, or Mg and Zn, and the following expressions (4) to (8) are satisfied:

$$k_{33} \geq 0.65 \quad (1)$$

$$\varepsilon_{33}^S \geq 1000 \quad (2)$$

$$E_c \geq 12 \quad (3)$$

$$0 \leq a2 \leq 0.1 \quad (4)$$

$$a1 + a2 = 1 \quad (5)$$

$$x + y + z = 1 \quad (6)$$

$$0.1 \leq x \leq 0.375 \quad (7)$$

$$0.5 \leq y/(y+z) \leq 0.64 \quad (8)$$

It is also much more effective that the piezoelectric composition include, as a main component, a composition represented by the following general formula, from the viewpoint of increasing the sensitivity to ultrasound.

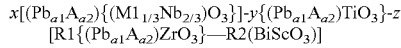

in which A represents Ba or Sr, M1 represents Mg, or Mg and Zn, and the following expressions are satisfied.

$$0 \leq a2 \leq 0.1$$

$$a1 + a2 = 1$$

$$x + y + z = 1$$

$$0.1 \leq x \leq 0.25$$

$$0.5 \leq y/(y+z) \leq 0.64$$

$$0 < R2 \leq 0.25.$$

It is more effective that the piezoelectric composition be ceramics oriented in a specific plane orientation from the viewpoint that high piezoelectric characteristics are exhibited as compared with a piezoelectric composition being isotropic ceramics, and it is also more effective that the piezoelectric composition be a single crystal having a specific plane orientation from the above viewpoint.

While there is described a case where the ultrasound probe according to the present Embodiment has the same configuration as that of ultrasound probe 100a according to Embodiment 1, the ultrasound probe according to Embodiment 4 is not limited thereto. The ultrasound probe according to Embodiment 4 can be adopted to an ultrasound probe having the configuration of any of the ultrasound probes according to Embodiments 2 and 3.

As disclosed in Japanese Patent No. 5063606 above, the necessity has been conventionally known for increases in free relative permittivity $\varepsilon_{33}^T$, electromechanical coupling coefficient $k_{33}$ and coercive electric field $E_c$ of a piezoelectric composition for an ultrasound probe. Japanese Patent No. 5063606, however, has disclosed not bound relative permittivity $\varepsilon_{33}^S$, but free relative permittivity $\varepsilon_{33}^T$. In addition, the maximum of $E_c$ disclosed in Examples of Japanese Patent No. 5063606 has been about 10 kV/cm. When the thickness of a piezoelectric body is low, a higher $E_c$ is desirable. The present inventors have found that the piezoelectric composition having the composition is adopted to thereby sufficiently increase all of $\varepsilon_{33}^S$, $E_c$ and $k_{33}$. The present inventors have further found that the PMN-PZT-based material can be replaced with a $BiScO_3$-based material to thereby impart higher $k_{33}$ in the polarization direction with high $\varepsilon_{33}^S$ being kept.

Japanese Patent Application Laid-Open No. 2006-188414 has disclosed a piezoelectric component for low-frequency articles such as a piezoelectric speaker and a piezoelectric pump as applications of a piezoelectric composition whose material is replaced with $BiScO_3$. Therefore, Japanese Patent Application Laid-Open No. 2006-188414 has focused on only the piezoelectric constant and the electromechanical coupling coefficient in a direction (lateral direction, direction 31) perpendicular to the polarization direction (electric field direction) of the piezoelectric composition. In the case of an array type ultrasound probe, the coupling coefficient in the lateral direction (direction 31) is desirably lower so that the ultrasound signals from adjacent piezoelectric elements are not mutually affected. Japanese Patent Application Laid-Open No. 2006-188414, however, has not focused on the bound relative permittivity and the electromechanical coupling coefficient in a direction (longitudinal direction, direction 33) parallel with the polarization direction (electric field direction) of the piezoelectric composition, such properties being necessary for the ultrasound probe. On the contrary, the present inventors have focused on $\varepsilon_{33}^S$ and $k_{33}$, and have found that the piezoelectric composition is adopted to thereby sufficiently increase all of $\varepsilon_{33}^S$, $E_c$ and $k_{33}$.

Embodiments 1 to 4 can provide a piezoelectric element and an ultrasound probe excellent in sensitivity to ultrasound even when a piezoelectric composition having a small thickness is adopted, and can provide an ultrasound imaging apparatus having the ultrasound probe.

EXAMPLES

Hereinafter, the present invention is described in more detail with reference to Examples.

[Simulation]

The simulation of the sensitivity to ultrasound in the changes of $k_{eff}$, $\varepsilon_{33}^S$ and $E_c$ was performed. An ultrasound probe here used for the simulation had a configuration in which a back surface load material having an acoustic impedance of 2.8 MRayl, a piezoelectric composition, four acoustic matching layers, and an acoustic lens were layered in the order presented. The impedance of a cable (length: 2.2 m) that connected the ultrasound probe and the main body of an ultrasound imaging apparatus was 75Ω, and the input-output impedance in transmitting and receiving was 50Ω. The simulation was performed under such configuration conditions according to a KLM (Krimholtz, Leedom and Mattaei model) method.

$k_{eff}$, $\varepsilon_{33}^S$ and $E_c$ were set as shown in Table 1, the output voltage $V_{out}$ was 100 V, and the simulation of the sensitivity to ultrasound was performed with respect to respective array type ultrasound probes whose configurations were the same as those of the ultrasound probes according to Embodiments 1 to 3.

The class, the ultrasound probe No., the ultrasound probe configuration, and the conditions and simulation results (sensitivity) of the simulation are shown Tables 1 to 3. In Tables 1 to 3, "No." represents the ultrasound probe number.

Table 1 shows the results for the ultrasound probe according to Embodiment 1. The title of Table 1 represents a "DML type ultrasound probe", and means that the simulation results with respect to an array type ultrasound probe having the configuration of the ultrasound probe according to Embodiment 1 are shown. The center frequency was set at 10 MHz. In the present Example, the DML type ultrasound probe was an ultrasound probe having the above configuration further including an acoustic back layer having an acoustic impedance of 94 MRayl between the back surface load material and the piezoelectric composition under the above configuration conditions. The following further conditions were added thereto: the pitch between channels arrayed was 0.2 mm and the opening width of each of the channels in the shorter axis direction was 3 mm. In Table 1, the "relative sensitivity" represents the sensitivity of each ultrasound probe with, as the reference (0), the sensitivity to ultrasound in a simulation under a condition where a commercially available soft material having good piezoelectric characteristics and a high $E_c$, C-6 (manufactured by Fuji Ceramics Corporation), was used as the material of the piezoelectric composition.

Table 2 shows the results for the ultrasound probe according to Embodiment 2. The title of Table 2 represents a "multi-layer type ultrasound probe", and means that the simulation results with respect to an array type ultrasound probe having the configuration of the ultrasound probe according to Embodiment 2 are shown. The center frequency was set at 7 MHz. The present simulation was performed under the same conditions as the above configuration conditions, and the number of piezoelectric composition layers was 3. The following further conditions were added thereto: the pitch between channels arrayed was 0.1 mm and the opening width of each of the channels in the shorter axis direction was 5 mm. In Table 2, the "relative sensitivity" represents the sensitivity of each ultrasound probe with, as the reference (0), the sensitivity to ultrasound in a simulation under a condition where a commercially available soft material having good piezoelectric characteristics and a high $\varepsilon_{33}^S$, C-83H (manufactured by Fuji Ceramics Corporation), was used as the material of the piezoelectric composition.

Table 3 shows the results for the ultrasound probe according to Embodiment 3. The title of Table 3 represents a "single-layer type ultrasound probe", and means that the simulation results with respect to an array type ultrasound probe having the configuration of the ultrasound probe according to Embodiment 3 are shown. The center frequency was set at 15 MHz. The present simulation was performed under the same conditions as the above configuration conditions. The following further conditions were added thereto: the pitch between channels arrayed was 0.2 mm and the opening width of each of the channels in the shorter axis direction was 2.5 mm. In Table 3, the "relative sensitivity" represents the sensitivity of each ultrasound probe with, as the reference (0), the sensitivity to ultrasound in a simulation under a condition where C-6 (manufactured by Fuji Ceramics Corporation) was used as the material of the piezoelectric composition and a single-layer piezoelectric plate was used.

TABLE 1

Simulation results with respect to DML type ultrasound probe

| Class | No. | $k_{eff}$ [—] | $\varepsilon_{33}^S$ [—] | $E_c$ [kV/cm] | Relative sensitivity [dB] |
|---|---|---|---|---|---|
| Example | 1 | 0.5 | 2200 | 18 | 1.2 |
| | 2 | 0.5 | 1700 | 18 | 0.5 |
| | 3 | 0.7 | 600 | 18 | 1.8 |
| | 4 | 0.9 | 600 | 18 | 3.6 |
| | 5 | 0.9 | 2200 | 18 | 8.2 |
| | 6 | 0.7 | 1200 | 18 | 5.3 |
| | 7 | 0.5 | 2200 | 15 | 1.0 |
| | 8 | 0.55 | 1400 | 15 | 1.3 |
| | 9 | 0.7 | 600 | 15 | 1.6 |
| | 10 | 0.9 | 600 | 15 | 3.4 |
| | 11 | 0.9 | 2200 | 15 | 8.0 |
| | 12 | 0.7 | 1400 | 15 | 5.7 |
| | 13 | 0.65 | 2200 | 10 | 2.0 |
| | 14 | 0.65 | 1400 | 10 | 0.8 |
| | 15 | 0.85 | 600 | 10 | 1.1 |
| | 16 | 0.9 | 1400 | 10 | 3.5 |
| | 17 | 0.9 | 2200 | 10 | 4.5 |
| | 18 | 0.75 | 1400 | 10 | 3.4 |
| | 19 | 0.75 | 2200 | 7 | 1.1 |
| | 20 | 0.75 | 1400 | 7 | 0.3 |
| | 21 | 0.9 | 1600 | 7 | 0.8 |
| Reference Example | R1 | 0.69 | 820 | 10.5 | 0 |
| Comparative Example | C1 | 0.5 | 1200 | 18 | −1.5 |
| | C2 | 0.6 | 600 | 18 | −2.2 |
| | C3 | 0.55 | 800 | 15 | −2.4 |
| | C4 | 0.55 | 2200 | 10 | −1.0 |
| | C5 | 0.6 | 1200 | 10 | −1.2 |
| | C6 | 0.7 | 600 | 10 | −2.0 |
| | C7 | 0.65 | 2200 | 7 | −1.1 |
| | C8 | 0.65 | 1400 | 7 | −2.3 |
| | C9 | 0.85 | 800 | 7 | −0.6 |

TABLE 2

Simulation results with respect to multi-layer type ultrasound probe

| Class | No. | $k_{eff}$ [—] | $\varepsilon_{33}^S$ [—] | $E_c$ [kV/cm] | Relative sensitivity [dB] |
|---|---|---|---|---|---|
| Example | 22 | 0.5 | 800 | 18 | 1.0 |
| | 23 | 0.5 | 2200 | 15 | 1.1 |
| | 24 | 0.5 | 1000 | 15 | 0.4 |
| | 25 | 0.65 | 2200 | 9 | 0.4 |
| | 26 | 0.65 | 1000 | 9 | 0.4 |
| | 27 | 0.75 | 600 | 9 | 0.9 |
| | 28 | 0.9 | 600 | 9 | 0.9 |
| | 29 | 0.9 | 2200 | 9 | 2.1 |
| | 30 | 0.8 | 2200 | 7 | 0.2 |
| | 31 | 0.8 | 800 | 7 | 0.6 |
| | 32 | 0.9 | 1000 | 7 | 0.1 |
| | 33 | 0.55 | 2200 | 15 | 2.5 |
| | 34 | 0.55 | 1400 | 15 | 2.7 |
| | 35 | 0.6 | 600 | 15 | 1.5 |
| | 36 | 0.65 | 2200 | 11 | 2.1 |
| | 37 | 0.65 | 1000 | 11 | 2.1 |
| | 38 | 0.75 | 600 | 9 | 0.9 |
| | 39 | 0.9 | 600 | 9 | 0.9 |
| | 40 | 0.5 | 2200 | 18 | 2.5 |
| | 41 | 0.9 | 600 | 18 | 6.7 |
| | 42 | 0.9 | 1400 | 18 | 8.4 |
| | 43 | 0.9 | 2200 | 18 | 8.0 |
| | 44 | 0.7 | 1200 | 18 | 7.7 |
| | 45 | 0.75 | 600 | 15 | 5.3 |
| | 46 | 0.9 | 600 | 15 | 5.3 |
| | 47 | 0.9 | 2200 | 15 | 6.5 |
| | 48 | 0.7 | 1400 | 15 | 6.3 |
| | 49 | 0.75 | 1400 | 9 | 2.8 |
| | 50 | 0.5 | 1400 | 18 | 2.3 |
| | 51 | 0.6 | 600 | 18 | 3.0 |
| | 52 | 0.5 | 2200 | 17 | 2.5 |
| | 53 | 0.5 | 1400 | 17 | 2.3 |
| | 54 | 0.6 | 600 | 17 | 3.0 |
| | 55 | 0.75 | 600 | 11 | 2.6 |
| | 56 | 0.9 | 600 | 11 | 2.6 |
| | 57 | 0.75 | 2200 | 9 | 2.4 |
| | 58 | 0.75 | 1000 | 9 | 2.4 |

TABLE 2-continued

Simulation results with respect to multi-layer type ultrasound probe

| Class | No. | $k_{eff}$ [—] | $\varepsilon_{33}{}^s$ [—] | $E_c$ [kV/cm] | Relative sensitivity [dB] |
|---|---|---|---|---|---|
| | 59 | 0.9 | 1000 | 9 | 2.2 |
| | 60 | 0.9 | 2200 | 9 | 2.2 |
| Reference Example | R2 | 0.70 | 1210 | 7 | 0 |
| Comparative Example | C10 | 0.55 | 600 | 13 | −1.3 |
| | C11 | 0.5 | 1400 | 13 | −0.4 |
| | C12 | 0.5 | 2200 | 13 | −0.2 |
| | C13 | 0.6 | 2200 | 9 | −0.8 |
| | C14 | 0.6 | 1200 | 9 | −0.6 |
| | C15 | 0.7 | 600 | 9 | −0.3 |
| | C16 | 0.7 | 2200 | 7 | −0.9 |
| | C17 | 0.65 | 1000 | 7 | −0.6 |
| | C18 | 0.8 | 600 | 7 | −0.3 |

TABLE 3

Simulation results with respect to single-layer type ultrasound probe

| Class | No. | $k_{eff}$ [—] | $\varepsilon_{33}{}^s$ [—] | $E_c$ [kV/cm] | Relative sensitivity [dB] |
|---|---|---|---|---|---|
| Example | 61 | 0.55 | 2200 | 18 | 1.3 |
| | 62 | 0.55 | 1400 | 18 | 0.2 |
| | 63 | 0.75 | 600 | 18 | 1.4 |
| | 64 | 0.9 | 600 | 18 | 1.1 |
| | 65 | 0.9 | 2200 | 18 | 5.2 |
| | 66 | 0.7 | 1200 | 18 | 3.8 |
| | 67 | 0.55 | 2200 | 13 | 1.3 |
| | 68 | 0.55 | 1400 | 13 | 0.2 |
| | 69 | 0.75 | 600 | 13 | 1.4 |
| | 70 | 0.9 | 600 | 13 | 1.1 |
| | 71 | 0.9 | 2200 | 13 | 5.2 |
| | 72 | 0.7 | 1400 | 13 | 4.4 |
| | 73 | 0.8 | 600 | 10 | 0.4 |
| | 74 | 0.85 | 600 | 10 | 0.7 |
| | 75 | 0.9 | 2200 | 10 | 3.3 |
| | 76 | 0.75 | 2200 | 7 | 1.0 |
| | 77 | 0.75 | 1400 | 7 | 0.3 |
| | 78 | 0.85 | 1200 | 7 | 0.3 |
| | 79 | 0.9 | 2200 | 7 | 0.2 |
| | 80 | 0.8 | 1600 | 7 | 1.2 |
| Reference Example | R3 | 0.69 | 820 | 10.5 | 0 |
| Comparative Example | C19 | 0.5 | 2000 | 13 | −0.7 |
| | C20 | 0.5 | 1400 | 13 | −0.9 |
| | C21 | 0.6 | 600 | 13 | −2.1 |
| | C22 | 0.55 | 2200 | 10 | −0.7 |

As shown in Table 1, ultrasound probes 1 to 21 according to Examples were excellent in sensitivity to ultrasound when compared with ultrasound probe R1 as a reference. The reason for this was considered because the piezoelectric composition of each of ultrasound probes 1 to 21 had piezoelectric characteristics possessed by a portion (see FIG. 2) surrounded by polyhedron 1 having point A1 to point A18 shown above as vertexes in Cartesian coordinates ($k_{eff}$, $\varepsilon_{33}{}^S$, $E_c$).

In contrast, ultrasound probes C1 to C9 according to Comparative Examples were insufficient in sensitivity to ultrasound when compared with ultrasound probe R1 as a reference. The reason for this was considered because the piezoelectric composition of each of ultrasound probes C1 to C9 did not have piezoelectric characteristics expressed by any coordinates included in a region formed by polyhedron 1 having point A1 to point A18 shown above as vertexes in Cartesian coordinates ($k_{eff}$, $\varepsilon_{33}{}^S$, $E_c$).

As shown in Table 2, ultrasound probes 22 to 60 according to Examples were excellent in sensitivity to ultrasound when compared with ultrasound probe R2 as a reference. The reason for this was considered because the piezoelectric composition of each of ultrasound probes 22 to 60 had piezoelectric characteristics possessed by a portion (see FIG. 5) surrounded by polyhedron 2 having point B1 to point B14 shown above as vertexes in Cartesian coordinates ($k_{eff}$, $\varepsilon_{33}{}^S$, $E_c$).

In particular, ultrasound probes 40 to 60 according to Examples had a relative sensitivity of 2.2 dB or more when compared with ultrasound probe R2 as a reference. The reason for this was considered because the piezoelectric composition of each of ultrasound probes 40 to 60 had piezoelectric characteristics possessed by a portion (see FIG. 6) surrounded by polyhedron 2' having point B51 to point B64 shown above as vertexes in ($k_{eff}$, $\varepsilon_{33}{}^S$, $E_c$).

In contrast, ultrasound probes C10 to C18 according to Comparative Examples were insufficient in sensitivity to ultrasound when compared with ultrasound probe R2 as a reference. The reason for this was considered because the piezoelectric composition of each of ultrasound probes C10 to C18 did not have piezoelectric characteristics expressed by any coordinates included in a region formed by polyhedron 2 having point B1 to point B18 shown above as vertexes in Cartesian coordinates ($k_{eff}$, $\varepsilon_{33}{}^S$, $E_c$).

As shown in Table 3, ultrasound probes 61 to 80 according to Examples were excellent in sensitivity to ultrasound when compared with ultrasound probe R3 as a reference. The reason for this was considered because the piezoelectric composition of each of ultrasound probes 61 to 80 had piezoelectric characteristics possessed by a portion (see FIG. 8) surrounded by polyhedron 3 having point C1 to point C18 shown above as vertexes in Cartesian coordinates ($k_{eff}$, $\varepsilon_{33}{}^S$, $E_c$).

In contrast, ultrasound probes C19 to C22 according to Comparative Examples were insufficient in sensitivity to ultrasound when compared with ultrasound probe R3 as a reference. The reason for this was considered because the piezoelectric composition of each of ultrasound probes C19 to C22 did not have piezoelectric characteristics expressed by any coordinates included in a region formed by polyhedron 3 having point C1 to point C18 shown above as vertexes in Cartesian coordinates ($k_{eff}$, $\varepsilon_{33}{}^S$, $E_c$).

[Production of Piezoelectric Element]

Next, there are described respective methods of producing a piezoelectric composition having any composition represented by the following general formula (1) or (2) and a piezoelectric element including, as a main component, the piezoelectric composition, the piezoelectric composition and the piezoelectric element being usable in the ultrasound probe according to the present invention. Also evaluated were piezoelectric characteristics ($d_{33}$, $k_{33}$, $\varepsilon_{33}{}^S$, $E_c$) of each piezoelectric element produced.

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\} \quad (1)$$

In the general formula (1), A represents Ba or Sr, M1 represents Mg, or Mg and Zn, and the following expressions are satisfied.

$$0 \leq a2 \leq 0.1$$

$$a1+a2=1$$

$$x+y+z=1$$

$$0.1 \leq x \leq 0.375$$

$$0.5 \leq y/(y+z) \leq 0.64$$

$$x[(Pb_{a1}A_{a2})\{(M1_{1/3}Nb_{2/3})O_3\}]\text{-}y\{(Pb_{a1}A_{a2})TiO_3\}\text{-}z[R1\{(Pb_{a1}A_{a2})ZrO_3\}\text{—}R2(BiScO_3)] \quad (2)$$

In the general formula (2), A represents Ba or Sr, M1 represents Mg, or Mg and Zn, and the following expressions are satisfied.

$$0 \leq a2 \leq 0.1$$

$$a1+a2=1$$

$$x+y+z=1$$

$$0.1 \leq x \leq 0.25$$

$$0.5 \leq y/(y+z) \leq 0.64$$

$$0 < R2 \leq 0.25$$

Hereinafter, bulk ceramics is described, but the piezoelectric composition in the present invention is particularly not limited to ceramics (polycrystal), and the present invention can also be applied to any case where the piezoelectric composition is oriented ceramics, a thick film, or a single crystal. When the piezoelectric composition is ceramics or a single crystal, such ceramics or single crystal may be cut to a desired size and then heat-treated.

[Production of Piezoelectric Element 1]

(Raw Material Preparation Step)

Respective powders of PbO, $BaCO_3$, $ZrO_2$, $TiO_2$ and $MgNb_2O_6$ were weighed in a ratio of x:y:z of 0.375:0.40:0.225 and a value of a2 of 0.05 in the general formula (1) so that the total amount was 30 g.

The powders, 80 mL of ethanol, and a proper amount of a $ZrO_2$ ball were placed into a pot, and the powders were pulverized by a ball mill for 16 hours. Next, the resulting mixed powder was calcined by heating at a furnace temperature of 800° C. for 6 hours. The resulting powder was further pulverized by a ball mill under the same conditions as above to provide calcined powder 1.

Three parts by mass of PVB based on 100 parts by mass of calcined powder 1 was added to calcined powder 1, mixed, and press-molded into a disc shape to provide molded product 1. Molded product 1 had a diameter of 12 mm and a height (thickness) of 1.5 mm.

(Heat Treatment Step)

Molded product 1 was placed into a crucible in order to inhibit raw material components from being volatilized from molded product 1, and the crucible furnace temperature was raised from room temperature to 1,250° C. at a rate of temperature rise of 200° C./hour. Next, molded product 1 was heated at a furnace temperature of 1,250° C. for 2 hours.

(Cooling Step)

Molded product 1 heat-treated was cooled to room temperature at a cooling rate of 0.05 to 0.3° C./second to provide molded product 1 subjected to heat treatment 1.

(Electrode Formation Step)

Piezoelectric composition 1 was polished, a gold electrode was disposed thereon by sputtering, and the resultant was cut by a diamond cutter to a desired size (4 mm×1.5 mm×0.4 mm).

(Polarization Step)

Next, a polarization treatment was performed in oil at 60° C. in an oil bath for 30 minutes by application of an electric field of 35 kV/cm for 30 minutes, to thereby provide piezoelectric element 1 for measurements of piezoelectric constant $d_{33}$ and coercive electric field $E_c$.

Piezoelectric composition 1 was cut to a size of 1 mm×1 mm×3 mm, a gold electrode was deposited on each of surfaces of the resultant, opposite to each other in the longitudinal direction, by sputtering, to thereby produce a piezoelectric element as a sample for measurements of electromechanical coupling coefficient $k_{33}$ and bound relative permittivity $\varepsilon_{33}^S$ described below. Piezoelectric element 1 for measurements of $k_{33}$ and $\varepsilon_{33}^S$ was also subjected to a polarization treatment in the same manner as in the polarization step.

[Evaluation]

(1) Measurement of Piezoelectric Constant $d_{33}$

Piezoelectric element 1 for measurement of $d_{33}$ was used to measure piezoelectric constant $d_{33}$ of piezoelectric composition 1 by a berlin court type $d_{33}$ meter, and $d_{33}$ of the piezoelectric element 1 was found to be 432 pC/N.

(2) Measurement of Electromechanical Coupling Coefficient $k_{33}$

Piezoelectric element 1 for measurement of $k_{33}$ was used to measure electromechanical coupling coefficient $k_{33}$ of piezoelectric composition 1 by an impedance analyzer (Agilent 4294A; manufactured by Agilent Technologies) according to a resonance-antiresonance method, and $k_{33}$ of piezoelectric element 1 was found to be 0.66.

(3) Measurement of Bound Relative Permittivity $\varepsilon_{33}^S$

Piezoelectric element 1 for measurement of $\varepsilon_{33}^S$ was used to measure bound relative permittivity $\varepsilon_{33}^S$ of piezoelectric composition 1 by the impedance analyzer at a frequency equal to or higher than the antiresonant frequency, and $\varepsilon_{33}^S$ of piezoelectric element 1 was found to be 1510.

(4) Measurement of Coercive Electric Field $E_c$

Piezoelectric element 1 for measurement of $E_c$ was used to measure coercive electric field $E_c$ of piezoelectric composition 1 by a charge amplifier type ferroelectric characteristic evaluation system (manufactured by Leadtech), and $E_c$ of piezoelectric element 1 was found to be 12 kV/cm.

[Production of Piezoelectric Elements 2 to 7]

Each of piezoelectric elements 2 to 7 was produced in the same manner as in piezoelectric element 1 except that respective powders of PbO, $BaCO_3$, $ZrO_2$, $TiO_2$ and $MgNb_2O_6$ were used so that the values of x, y, z and a2 were as shown in Table 4 below, and piezoelectric characteristics thereof were evaluated in the same manner as in piezoelectric element 1.

[Production of Piezoelectric Elements 8 and 9]

Piezoelectric element 8 was produced in the same manner as in piezoelectric element 2 except that a powder of $SrCO_3$ was used instead of $BaCO_3$ so that Ba as A in the general formula (1) was replaced with Sr, and piezoelectric characteristics thereof were evaluated in the same manner as in piezoelectric element 1. In addition, piezoelectric element 9 was produced in the same manner as in piezoelectric element 3 except that a powder of $SrCO_3$ was used instead of $BaCO_3$ so that Ba as A was replaced with Sr, and piezoelectric characteristics thereof were evaluated in the same manner as in piezoelectric element 1.

[Production of Piezoelectric Elements 10 to 13]

Each of piezoelectric element 10 to 13 was produced in the same manner as in piezoelectric element 1 except that respective powders of PbO, $Bi_2O_3$, $BaCO_3$, $ZrO_2$, $TiO_2$, $MgNb_2O_6$ and $Sc_2CO_3$ were used so that the values of x, y, z and a2 were as shown in Table 4 below and R2 in the general formula (2) represented each value as shown in Table 4 below, and piezoelectric characteristics thereof were evaluated in the same manner as in piezoelectric element 1.

In production of each of piezoelectric elements 2 to 13, the polarization treatment temperature was in the range from 40 to 150° C., the voltage to be applied was in the range from 10 to 40 kV/cm and the voltage application time was in the range from 10 to 60 minutes.

The class, x, y, z, y/(y+z), a2, R2, element A, $d_{33}$, $k_{33}$, $\varepsilon_{33}^S$ and $E_c$ with respect to piezoelectric elements 1 to 13 are shown in Table 4. In Table 4, "No." represents the piezoelectric element No.

TABLE 4

| No. | x | y | z | y/(y + z) | a2 | R2 | A | $d_{33}$ [pC/N] | $k_{33}$ [—] | $\varepsilon_{33}^s$ [—] | $E_c$ [kV/cm] |
|---|---|---|---|---|---|---|---|---|---|---|---|
| 1 | 0.375 | 0.40 | 0.225 | 0.64 | 0.05 | 0 | Ba | 432 | 0.66 | 1510 | 12.0 |
| 2 | 0.25 | 0.42 | 0.33 | 0.56 | 0.05 | 0 | Ba | 505 | 0.69 | 1100 | 12.1 |
| 3 | 0.20 | 0.43 | 0.37 | 0.538 | 0.05 | 0 | Ba | 460 | 0.72 | 1120 | 13.5 |
| 4 | 0.20 | 0.43 | 0.37 | 0.538 | 0.07 | 0 | Ba | 516 | 0.71 | 1230 | 12.9 |
| 5 | 0.20 | 0.44 | 0.36 | 0.55 | 0.07 | 0 | Ba | 420 | 0.67 | 1130 | 15.0 |
| 6 | 0.15 | 0.44 | 0.41 | 0.518 | 0.07 | 0 | Ba | 550 | 0.72 | 1140 | 13.0 |
| 7 | 0.15 | 0.45 | 0.40 | 0.529 | 0.07 | 0 | Ba | 400 | 0.67 | 1060 | 15.4 |
| 8 | 0.25 | 0.42 | 0.33 | 0.56 | 0.05 | 0 | Sr | 524 | 0.70 | 1250 | 12.5 |
| 9 | 0.20 | 0.43 | 0.37 | 0.538 | 0.05 | 0 | Sr | 480 | 0.71 | 1150 | 13.0 |
| 10 | 0.10 | 0.48 | 0.42 | 0.533 | 0.05 | 0.25 | Ba | 572 | 0.72 | 1100 | 13.1 |
| 11 | 0.15 | 0.46 | 0.39 | 0.541 | 0.05 | 0.12 | Ba | 440 | 0.68 | 1080 | 15.8 |
| 12 | 0.15 | 0.465 | 0.385 | 0.547 | 0.05 | 0.25 | Ba | 599 | 0.72 | 1150 | 13.0 |
| 13 | 0.20 | 0.44 | 0.36 | 0.55 | 0.05 | 0.12 | Ba | 563 | 0.73 | 1130 | 12.0 |

As can be seen from Table 4, all piezoelectric elements 1 to 13 satisfy the following expressions. In consideration of the $k_{eff}$ value being about $0.9 \times k_{33}$ to $1 \times k_{33}$, all piezoelectric elements 1 to 13 fall within the conditions with respect to all of polyhedron 1, polyhedron 2, polyhedron 2' and polyhedron 3. That is, piezoelectric elements 1 to 13 including, as a main component, the composition represented by general formula (1) or (2) are each found to be a material effective for any ultrasound probes having the same configuration as the ultrasound probes according to Embodiments 1 to 3.

$$k_{33} \geq 0.65$$

$$\varepsilon_{33}^S \geq 1000$$

$$E_c \geq 12$$

When piezoelectric characteristics of piezoelectric element 2 and those of piezoelectric element 8 are compared, and piezoelectric characteristics of piezoelectric element 3 and those of piezoelectric element 9 are compared, it can be seen that there are not any remarkable differences in piezoelectric characteristics whether element A represents Ba or Sr. That is, it can be seen that piezoelectric elements 1 to 13 including, the composition represented by general formula (1) or (2) are each a material effective for any ultrasound probe having the same configuration as the ultrasound probes according to Embodiments 1 to 3, whether element A represents Ba or Sr.

Furthermore, when piezoelectric characteristics of piezoelectric elements 1 to 9 and piezoelectric characteristics of piezoelectric elements 10 to 13 are mutually compared, it can be seen that, when R2 is more than 0, the $d_{33}$ and $k_{33}$ values are increased with $\varepsilon_{33}^S$ being kept at the same level. That is, $BiScO_3$ is preferably introduced to the piezoelectric composition from the viewpoint of enhancing piezoelectric characteristics of the piezoelectric composition in the polarization direction, such characteristics being important for the ultrasound probe. In the present Example, the amounts of Ba and Sr serving as A replaced can be 0. M1 can also be partially replaced with Zn.

INDUSTRIAL APPLICABILITY

The present invention enables to form a high-sensitive ultrasound probe in the case of a piezoelectric composition having a small thickness. Accordingly, the present invention allows an ultrasound imaging apparatus to be expected to be further generally used.

What is claimed is:
1. An ultrasound probe comprising:
  a piezoelectric element comprising a piezoelectric composition and an electrode that applies a voltage to the piezoelectric composition, and
  an acoustic back layer acoustically coupled to the piezoelectric element and disposed on a back surface of the piezoelectric element, wherein
  the piezoelectric composition has piezoelectric characteristics expressed by any coordinates included in a region formed by a polyhedron having point A1 to point A18 shown below as vertexes in Cartesian coordinates ($k_{eff}$, $\varepsilon_{33}^S$, $E_c$) comprising variables $k_{eff}$, $\varepsilon_{33}^S$ and $E_c$ when an effective electromechanical coupling coefficient, a bound relative permittivity and a coercive electric field thereof are defined as $k_{eff}$, $\varepsilon_{33}^S$ and $E_c$ (kV/cm), respectively:
  Point A1 (0.5, 2200, 18)
  Point A2 (0.5, 1400, 18)
  Point A3 (0.7, 600, 18)
  Point A4 (0.9, 600, 18)
  Point A5 (0.9, 2200, 18)
  Point A6 (0.5, 2200, 15)
  Point A7 (0.5, 1400, 15)
  Point A8 (0.7, 600, 15)
  Point A9 (0.9, 600, 15)
  Point A10 (0.65, 2200, 10)
  Point A11 (0.65, 1400, 10)
  Point A12 (0.8, 600, 10)
  Point A13 (0.9, 600, 10)
  Point A14 (0.75, 2200, 7)
  Point A15 (0.75, 1400, 7)
  Point A16 (0.8, 1000, 7)
  Point A17 (0.9, 1000, 7)
  Point A18 (0.9, 2200, 7).

2. The ultrasound probe according to claim 1, wherein the ultrasound probe has a center frequency of a transmitting and receiving band of 7 MHz or more.

3. The ultrasound probe according to claim 1, wherein the piezoelectric composition satisfies the following expressions when an electromechanical coupling coefficient, a bound relative permittivity and a coercive electric field thereof are defined as $k_{33}$, $\varepsilon_{33}^S$ and $E_c$ (kV/cm), respectively:

$$k_{33} \geq 0.65;$$

$$\varepsilon_{33}^S \geq 1000; \text{ and}$$

$$E_c \geq 12.$$

4. The ultrasound probe according to claim 3, wherein a composition as a main component of the piezoelectric composition is represented by the following general formula:

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\}$$

wherein A represents Ba or Sr, M1 represents Mg, or Mg and Zn, and the following expressions are satisfied:

$$0 \leq a2 \leq 0.1;$$

$$a1 + a2 = 1;$$

$$x + y + z = 1;$$

$$0.1 \leq x \leq 0.375; \text{ and}$$

$$0.5 \leq y/(y+z) \leq 0.64.$$

5. The ultrasound probe according to claim 4, wherein a composition as a main component of the piezoelectric composition is represented by the following general formula:

$$x[(Pb_{a1}A_{a2})\{(M1_{1/3}Nb_{2/3})O_3\}]\text{-}y\{(Pb_{a1}A_{a2})TiO_3\}\text{-}z[R1\{(Pb_{a1}A_{a2})ZrO_3\}\text{—}R2(BiScO_3)]$$

wherein A represents Ba or Sr, M1 represents Mg, or Mg and Zn, and the following expressions are satisfied:

$$0 \leq a2 \leq 0.1;$$

$$a1 + a2 = 1;$$

$$x + y + z = 1;$$

$$0.1 \leq x \leq 0.25;$$

$$0.5 \leq y/(y+z) \leq 0.64; \text{ and}$$

$$0 < R2 \leq 0.25.$$

6. An ultrasound probe comprising:
a piezoelectric element comprising a plurality of piezoelectric compositions and an electrode that applies a voltage to each of the plurality of piezoelectric compositions, a layer of each of the piezoelectric compositions and the electrode being alternately stacked, wherein
the piezoelectric composition has piezoelectric characteristics expressed by any coordinates included in a region formed by a polyhedron having point B1 to point B14 shown below as vertexes in Cartesian coordinates ($k_{eff}$, $\varepsilon_{33}^S$, $E_c$) comprising variables $k_{eff}$, $\varepsilon_{33}^S$ and $E_c$ when an effective electromechanical coupling coefficient, a bound relative permittivity and a coercive electric field thereof are defined as $k_{eff}$, $\varepsilon_{33}^S$ and $E_c$ (kV/cm), respectively:

Point B1 (0.5, 2200, 18)
Point B2 (0.5, 600, 18)
Point B3 (0.9, 600, 18)
Point B4 (0.9, 2200, 18)
Point B5 (0.5, 2200, 15)
Point B6 (0.5, 600, 15)
Point B7 (0.65, 2200, 9)
Point B8 (0.65, 1000, 9)
Point B9 (0.75, 600, 9)
Point B10 (0.9, 600, 9)
Point B11 (0.8, 2200, 7)
Point B12 (0.8, 1000, 7)
Point B13 (0.9, 1000, 7)
Point B14 (0.9, 2200, 7).

7. The ultrasound probe according to claim 6, wherein the piezoelectric composition has piezoelectric characteristics expressed by any coordinates included in a region formed by a polyhedron having point B51 to point B64 shown below as vertexes:

Point B51 (0.5, 2200, 18)
Point B52 (0.5, 1400, 18)
Point B53 (0.6, 600, 18)
Point B54 (0.9, 600, 18)
Point B55 (0.9, 2200, 18)
Point B56 (0.5, 2200, 17)
Point B57 (0.5, 1400, 17)
Point B58 (0.6, 600, 17)
Point B59 (0.75, 600, 11)
Point B60 (0.9, 600, 11)
Point B61 (0.75, 2200, 9)
Point B62 (0.75, 1000, 9)
Point B63 (0.9, 1000, 9)
Point B64 (0.9, 2200, 9).

8. The ultrasound probe according to claim 6, wherein the ultrasound probe has a center frequency of a transmitting and receiving band of 7 MHz or more.

9. The ultrasound probe according to claim 6, wherein the piezoelectric composition satisfies the following expressions when an electromechanical coupling coefficient, a bound relative permittivity and a coercive electric field thereof are defined as $k_{33}$, $\varepsilon_{33}^S$ and $E_c$ (kV/cm), respectively:

$$k_{33} \geq 0.65;$$

$$\varepsilon_{33}^S \geq 1000; \text{ and}$$

$$E_c \geq 12.$$

10. The ultrasound probe according to claim 9, wherein a composition as a main component of the piezoelectric composition is represented by the following general formula:

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\}$$

wherein A represents Ba or Sr, M1 represents Mg, or Mg and Zn, and the following expressions are satisfied:

$$0 \leq a2 \leq 0.1;$$

$$a1 + a2 = 1;$$

$$x + y + z = 1;$$

$$0.1 \leq x \leq 0.375; \text{ and}$$

$$0.5 \leq y/(y+z) \leq 0.64.$$

11. The ultrasound probe according to claim 10, wherein the composition as a main component of the piezoelectric composition is represented by the following general formula:

$$x[(Pb_{a1}A_{a2})\{(M1_{1/3}Nb_{2/3})O_3\}]\text{-}y\{(Pb_{a1}A_{a2})TiO_3\}\text{-}z[R1\{(Pb_{a1}A_{a2})ZrO_3\}\text{—}R2(BiScO_3)]$$

wherein A represents Ba or Sr, M1 represents Mg, or Mg and Zn, and the following expressions are satisfied:

$0 \leq a2 \leq 0.1;$ $a1+a2=1;$ $x+y+z=1;$ $0.1 \leq x \leq 0.25;$ $0.5 \leq y/(y+z) \leq 0.64;$ and $0 < R2 \leq 0.25.$

12. An ultrasound probe comprising:
a piezoelectric element comprising a single-layer piezoelectric composition and an electrode that applies a voltage to the piezoelectric composition; and
no acoustic back layer to be acoustically coupled to the piezoelectric element and disposed on a back surface of the piezoelectric element, wherein
the piezoelectric composition has piezoelectric characteristics expressed by any coordinates included in a region formed by a polyhedron having point C1 to point C18 shown below as vertexes in Cartesian coordinates ($k_{eff}$, $\varepsilon_{33}^S$, $E_c$) comprising variables $k_{eff}$, $\varepsilon_{33}^S$ and $E_c$ when an effective electromechanical coupling coefficient, a bound relative permittivity and a coercive electric field thereof are defined as $k_{eff}$, $\varepsilon_{33}^S$ and $E_c$ (kV/cm), respectively:
Point C1 (0.55, 2200, 18)
Point C2 (0.55, 1400, 18)
Point C3 (0.75, 600, 18)
Point C4 (0.9, 600, 18)
Point C5 (0.9, 2200, 18)
Point C6 (0.55, 2200, 13)
Point C7 (0.55, 1400, 13)
Point C8 (0.75, 600, 13)
Point C9 (0.9, 600, 13)
Point C10 (0.6, 2200, 10)
Point C11 (0.6, 1400, 10)
Point C12 (0.8, 600, 10)
Point C13 (0.9, 600, 10)
Point C14 (0.75, 2200, 7)
Point C15 (0.75, 1400, 7)
Point C16 (0.8, 1200, 7)
Point C17 (0.9, 1200, 7)
Point C18 (0.9, 2200, 7).

13. The ultrasound probe according to claim 12, wherein a thickness of the piezoelectric composition is 0.02 to 1 mm.

14. The ultrasound probe according to claim 12, wherein the ultrasound probe has a center frequency of a transmitting and receiving band of 7 MHz or more.

15. The ultrasound probe according to claim 12, wherein the piezoelectric composition satisfies the following expressions when an electromechanical coupling coefficient, a bound relative permittivity and a coercive electric field thereof are defined as $k_{33}$, $\varepsilon_{33}^S$ and $E_c$ (kV/cm), respectively:

$k_{33} \geq 0.65;$ $\varepsilon_{33}^S \geq 1000;$ and $E_c \geq 12.$

16. The ultrasound probe according to claim 15, wherein a composition as a main component of the piezoelectric composition is represented by the following general formula:

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\}$$

wherein A represents Ba or Sr, M1 represents Mg, or Mg and Zn, and the following expressions are satisfied:

$0 \leq a2 \leq 0.1;$ $a1+a2=1;$ $x+y+z=1;$ $0.1 \leq x \leq 0.375;$ and $0.5 \leq y/(y+z) \leq 0.64.$

17. The ultrasound probe according to claim 16, wherein the composition as a main component of the piezoelectric composition is represented by the following general formula:

$$x[(Pb_{a1}A_{a2})\{(M1_{1/3}Nb_{2/3})O_3\}]\text{-}y\{(Pb_{a1}A_{a2})TiO_3\}\text{-}z[R1\{(Pb_{a1}A_{a2})ZrO_3\}\text{—}R2(BiScO_3)]$$

wherein A represents Ba or Sr, M1 represents Mg, or Mg and Zn, and the following expressions are satisfied:

$0 \leq a2 \leq 0.1;$ $a1+a2=1;$ $x+y+z=1;$ $0.1 \leq x \leq 0.25;$ $0.5 \leq y/(y+z) \leq 0.64;$ and $0 < R2 \leq 0.25.$

18. A piezoelectric element comprising:
a piezoelectric composition comprising, as a main component, a composition represented by the following general formula, and an electrode that applies a voltage to the piezoelectric composition, wherein
the piezoelectric composition satisfies the following expressions (1) to (3) when an electromechanical coupling coefficient, a bound relative permittivity and a coercive electric field thereof are defined as $k_{33}$, $\varepsilon_{33}^S$ and $E_c$ (kV/cm), respectively:

$$x[(Pb_{a1}A_{a2})\{(M1_{1/3}Nb_{2/3})O_3\}]\text{-}y\{(Pb_{a1}A_{a2})TiO_3\}\text{-}z\{(Pb_{a1}A_{a2})ZrO_3\}$$

wherein A represents Ba or Sr, M1 represents Mg, or Mg and Zn, and the following expressions (4) to (8) are satisfied:

$k_{33} \geq 0.65$ \hfill (1)

$\varepsilon_{33}^S \geq 1000$ \hfill (2)

$E_c \geq 12$ \hfill (3)

$0 \leq a2 \leq 0.1$ \hfill (4)

$a1+a2=1$ \hfill (5)

$x+y+z=1$ \hfill (6)

$0.1 \leq x \leq 0.375$ (7)

$0.5 \leq y/(y+z) \leq 0.64$ (8).

19. The piezoelectric element according to claim 18, wherein the piezoelectric composition comprises, as a main component, a composition represented by the following general formula:

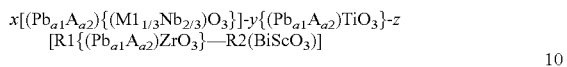

$x[(Pb_{a1}A_{a2})\{(M1_{1/3}Nb_{2/3})O_3\}]\text{-}y\{(Pb_{a1}A_{a2})TiO_3\}\text{-}z[R1\{(Pb_{a1}A_{a2})ZrO_3\}\text{—}R2(BiScO_3)]$ wherein A represents Ba or Sr, M1 represents Mg, or Mg and Zn, and the following expressions are satisfied:

$0 \leq a2 \leq 0.1$;

$a1+a2=1$;

$x+y+z=1$;

$0.1 \leq x \leq 0.25$;

$0.5 \leq y/(y+z) \leq 0.64$; and $0 < R2 \leq 0.25$.

20. An ultrasound probe comprising the piezoelectric element according to claim 18.

* * * * *